(12) United States Patent
Ogawa et al.

(10) Patent No.: US 10,660,720 B2
(45) Date of Patent: May 26, 2020

(54) SURGICAL-MANIPULATOR OPERATING DEVICE AND SURGICAL-MANIPULATOR SYSTEM

(71) Applicant: OLYMPUS CORPORATION, Tokyo (JP)

(72) Inventors: Ryohei Ogawa, Tokyo (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 565 days.

(21) Appl. No.: 15/374,139

(22) Filed: Dec. 9, 2016

(65) Prior Publication Data
US 2017/0086933 A1 Mar. 30, 2017

Related U.S. Application Data

(63) Continuation of application No. PCT/JP2015/062865, filed on Apr. 28, 2015.

(30) Foreign Application Priority Data

Jun. 17, 2014 (JP) ................. 2014-124462

(51) Int. Cl.
*A61B 34/00* (2016.01)
*B25J 3/00* (2006.01)
(Continued)

(52) U.S. Cl.
CPC .......... *A61B 34/74* (2016.02); *A61B 1/00133* (2013.01); *A61B 17/00* (2013.01);
(Continued)

(58) Field of Classification Search
CPC combination set(s) only.
See application file for complete search history.

(56) References Cited

U.S. PATENT DOCUMENTS 7,387,606 B2 * 6/2008 Weinberg ................. A61B 1/31
600/114
7,860,536 B2 12/2010 Jobs et al.
(Continued)

FOREIGN PATENT DOCUMENTS

EP 1 584 300 A1 10/2005
EP 3 111 879 A1 1/2017
(Continued)

OTHER PUBLICATIONS

International Search Report dated Jul. 21, 2015 issued in PCT/JP2015/062865.
(Continued)

*Primary Examiner* — Michael W Kahelin
*Assistant Examiner* — Shirley X Jian
(74) *Attorney, Agent, or Firm* — Scully, Scott, Murphy & Presser, P.C.

(57) ABSTRACT

A device for operating a surgical manipulator including, at a distal end of an elongate shaft: a rotational joint that is rotatable about a longitudinal axis of the shaft; and a flexing joint that is on a distal-end side of the rotational joint and that can be flexed about an axis that intersects the longitudinal axis. A surgical-manipulator operating device including: a gripping portion that is gripped by an operator; a rotation input portion that is provided with a rotating member attached to the gripping portion in a rotatable manner and with which rotation instructions for the rotational joint are input in accordance with rotational angles of the rotating member; and flexion input portions with which flexion instructions for the flexing joint are input in directions corresponding to fixed circumferential-direction operating positions on the rotating member.

8 Claims, 28 Drawing Sheets

(51) Int. Cl.
B25J 13/02 (2006.01)
A61B 17/00 (2006.01)
A61B 90/00 (2016.01)
A61B 1/00 (2006.01)
A61B 46/10 (2016.01)

(52) U.S. Cl.
CPC .............. *A61B 46/10* (2016.02); *A61B 90/00* (2016.02); *B25J 3/00* (2013.01); *B25J 13/02* (2013.01); *A61B 1/00128* (2013.01); *A61B 17/00234* (2013.01)

(56) References Cited

U.S. PATENT DOCUMENTS

| | | | | |
|---|---|---|---|---|
| 8,425,405 | B2* | 4/2013 | Mitani | A61B 1/00114 |
| | | | | 348/65 |
| 8,480,703 | B2* | 7/2013 | Nicholas | A61B 17/07207 |
| | | | | 606/205 |
| 10,182,812 | B1* | 1/2019 | Ashraf | A61B 17/062 |
| 10,258,420 | B2* | 4/2019 | Ogawa | A61B 34/70 |
| 2003/0018237 | A1* | 1/2003 | Okada | A61B 1/00039 |
| | | | | 600/146 |
| 2003/0109857 | A1 | 6/2003 | Sanchez et al. | |
| 2005/0222587 | A1 | 10/2005 | Jinno et al. | |
| 2006/0155262 | A1* | 7/2006 | Kishi | A61B 34/70 |
| | | | | 606/1 |
| 2007/0100201 | A1 | 5/2007 | Komiya et al. | |
| 2009/0105726 | A1 | 4/2009 | Sugiyama | |
| 2009/0112060 | A1 | 4/2009 | Sugiyama et al. | |
| 2010/0022837 | A1 | 1/2010 | Ishiguro et al. | |
| 2011/0015569 | A1 | 1/2011 | Kirschenman et al. | |
| 2011/0237010 | A1* | 9/2011 | Lee | H01L 27/1248 |
| | | | | 438/34 |
| 2011/0238010 | A1* | 9/2011 | Kirschennnan | A61M 25/0105 |
| | | | | 604/95.04 |
| 2012/0130420 | A1 | 5/2012 | Nicholas et al. | |
| 2016/0324589 | A1* | 11/2016 | Ogawa | A61B 34/70 |
| 2016/0354170 | A1 | 12/2016 | Ogawa et al. | |
| 2017/0325903 | A1* | 11/2017 | Nichogi | B25J 1/08 |

FOREIGN PATENT DOCUMENTS

| | | |
|---|---|---|
| JP | H05-192348 A | 8/1993 |
| JP | H10-262900 A | 10/1998 |
| JP | 2003-010099 A | 1/2003 |
| JP | 2005-511334 A | 4/2005 |
| JP | 2005-312919 A | 11/2005 |
| JP | 2007-125180 A | 5/2007 |
| JP | 2008-264253 A | 11/2008 |
| JP | 2009-101077 A | 5/2009 |
| JP | 2012-110675 A | 6/2012 |
| JP | 2012-513845 A | 6/2012 |
| JP | 5011060 B2 | 8/2012 |
| JP | 2013-188323 A | 9/2013 |
| JP | 2013-206662 A | 10/2013 |
| JP | 2015-024037 A | 2/2015 |
| JP | 2015-157026 A | 9/2015 |
| WO | WO 2003/049910 A2 | 6/2003 |
| WO | WO 2010/078344 A1 | 7/2010 |

OTHER PUBLICATIONS

Extended Supplementary European Search Report dated Jan. 5, 2018 in European Patent Application No. 15 80 9788.1.

* cited by examiner

SURGICAL-MANIPULATOR OPERATING DEVICE AND SURGICAL-MANIPULATOR SYSTEM

CROSS-REFERENCE TO RELATED APPLICATIONS

This is a continuation of International Application PCT/JP2015/062865 which is hereby incorporated by reference herein in its entirety.

This application is based on Japanese Patent Application No. 2014-124462, the contents of which are incorporated herein by reference.

TECHNICAL FIELD

The present invention relates to a surgical-manipulator operating device and a surgical-manipulator system.

BACKGROUND ART

In the related art, there is a known surgical-manipulator system that employs a master-slave system and with which an electrical surgical manipulator that has two joints at a distal end of an elongate shaft introduced into a body via an endoscope channel is operated by using an operating device that is constituted of a joystick (for example, see Patent Literature 1).

CITATION LIST

Patent Literature

{PTL 1} Japanese Unexamined Patent Application, Publication No. 2009-101077

SUMMARY OF INVENTION

Solution to Problem

An aspect of the present invention provides a surgical-manipulator operating device that is a device for operating a surgical manipulator provided with, at a distal end of an elongate shaft, a rotational joint that is rotatable about a longitudinal axis of the shaft, and a flexing joint that is on a distal-end side of the rotational joint and that can be flexed about an axis that intersects the longitudinal axis, the surgical-manipulator operating device including: a gripping portion that is gripped by an operator; a rotation input portion that is provided with a rotating member attached to the gripping portion in a rotatable manner and with which rotation instructions for the rotational joint are input in accordance with rotational angles of the rotating member; and a flexion input portion with which flexion instructions for the flexing joint are input in directions corresponding to fixed circumferential-direction operating positions on the rotating member.

DESCRIPTION OF EMBODIMENT

A surgical-manipulator system 1 according to an embodiment of the present invention will be described below with reference to the drawings.

Figure 1:
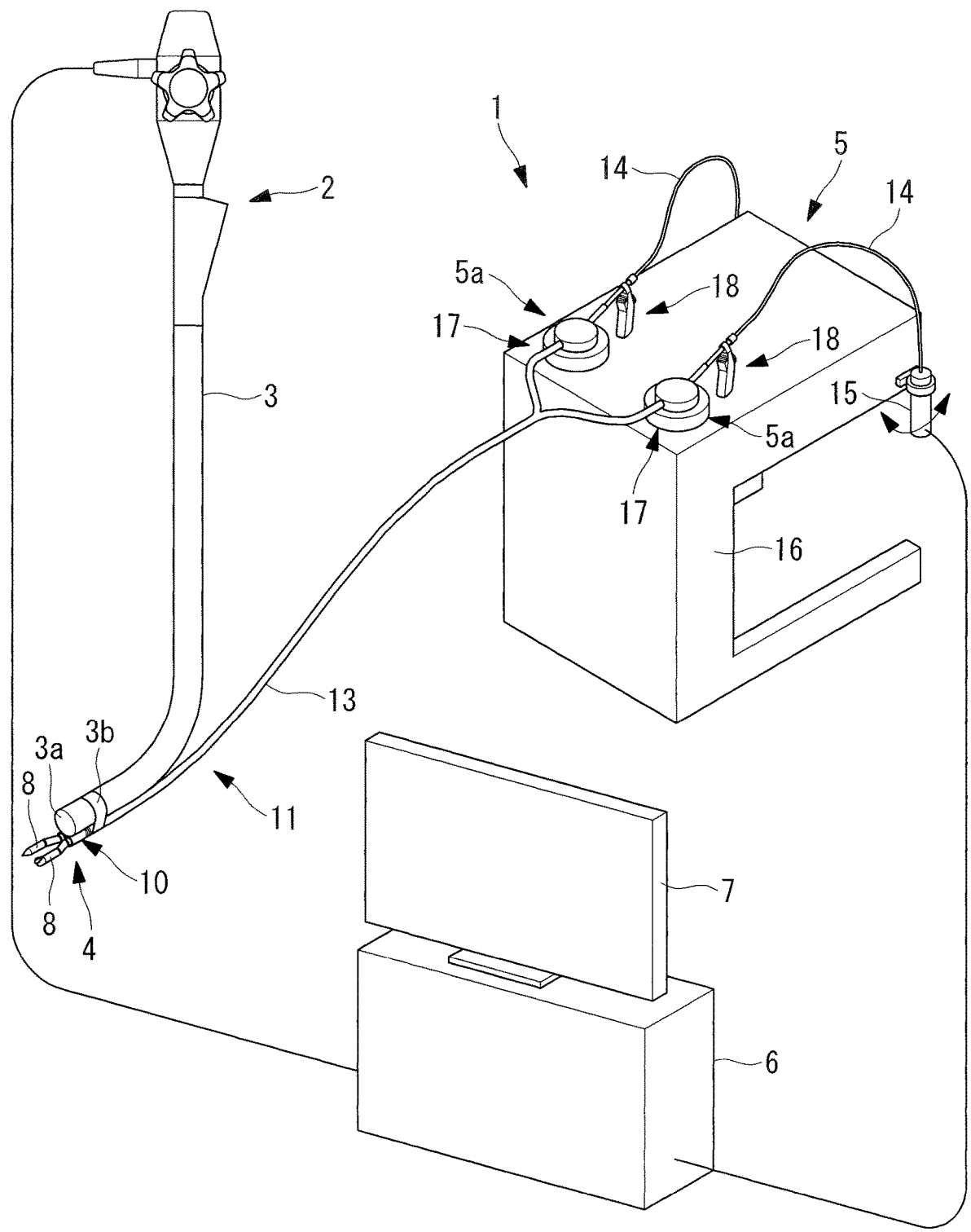
FIG. 1 is an overall configuration diagram showing a surgical-manipulator system according to an embodiment of the present invention.

As shown in FIG. 1, the surgical-manipulator system 1 according to this embodiment is provided with: a manipulator 4 that is actuated by being secured, by means of a belt-like securing tool 3b, to a distal-end portion of an inserted portion 3 of a flexible endoscope 2; a manipulator-operating portion 5 for operating the manipulator 4; a control portion 6 that controls the manipulator 4 on the basis of operating instructions that are input via the manipulator-operating portion 5; and a monitor 7 that displays images acquired by using the flexible endoscope 2.

The manipulator 4 is provided with: two multi-joint treatment tools 8 that are disposed in a state in which the multi-joint treatment tools 8 protrude forward from a distal-end surface 3a of the inserted portion 3 into a viewing-field area of the flexible endoscope 2; a moving mechanism 10 for moving the individual multi-joint treatment tools 8 as a whole; and a multi-joint-treatment-tool driving mechanism 11 for electrically moving the individual multi-joint treatment tools 8. The multi-joint treatment tools 8 each have a rotational joint 8a that is electrically operated and a flexing joint 8b that is disposed farther on the distal-end side than the rotational joint 8a is and is provided with, at the distal ends thereof, end effectors 12 such as gripping forceps, energy forceps, or the like.

The moving mechanism 10 is provided with bending arms (not shown) that cause the individual multi-joint treatment tools 8 to pivot in predetermined directions. In addition, the moving mechanism 10 supports the multi-joint treatment tools 8 so as to be movable in directions in which the multi-joint treatment tools 8 are advanced and retracted with respect to the bending arms.

By doing so, the moving mechanism 10 can change the direction of the multi-joint treatment tools 8 as a whole by pivoting the bending arms in the predetermined directions, and the end effectors 12 at the distal ends thereof can be moved forward or backward in the viewing-field area of the flexible endoscope 2 by moving the multi-joint treatment tools 8 forward or backward as a whole by moving the multi-joint treatment tools 8 in the directions in which the multi-joint treatment tools 8 are advanced or retracted with respect to the bending arms.

An elongate and soft guide tube 13 is connected at a proximal-end side of the bending arms of the moving mechanism 10. A plurality of wires (not shown) pass through the guide tube 13 over the entire length thereof. Distal ends of the wires are connected to the bending arms so as to pivot the bending arms by means of tensile forces therein. Proximal ends of the wires are connected to the manipulator-operating portion 5 (described later) disposed on a proximal-end side of the guide tube 13.

Elongate and soft flexible portions (shafts) 14 are individually connected to the multi-joint treatment tools 8 on the proximal-end sides thereof. A plurality of wires (not shown) for driving the joints 8a and 8b of the individual multi-joint treatment tools 8 pass through the individual flexible portions 14 over the entire lengths thereof. Distal ends of the wires are connected to the individual joints 8a and 8b so as to independently drive the individual joints 8a and 8b by means of tensile forces therein.

Figure 2:
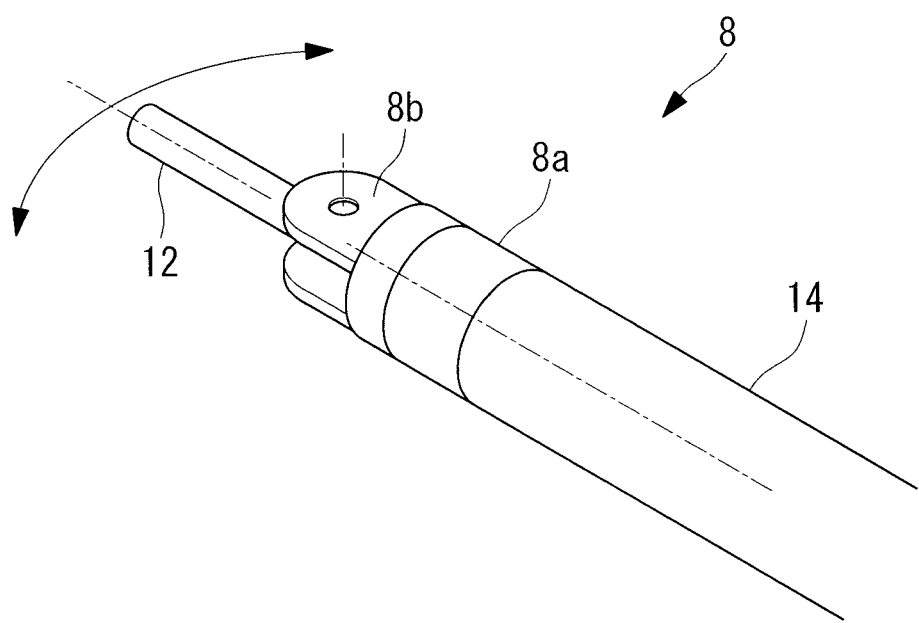
FIG. 2 is a perspective view showing, in outline, the configuration of a surgical manipulator employed in the surgical-manipulator system in FIG. 1.

Here, in describing this embodiment, the multi-joint treatment tools 8 will be described by showing, in outline, example structures thereof in FIG. 2. The rotational joints 8a of the multi-joint treatment tools 8 are provided so as to be rotatable about the longitudinal axes of the flexible portions 14. In addition, the flexing joints 8b of the multi-joint treatment tools 8 are attached on the distal-end sides of the rotational joints 8a and are configured so as to pivot the end effectors 12 about axes that are orthogonal to the longitudinal axes of the flexible portions 14.

In addition, the flexible portions 14 are connected to motor units 15 on the proximal-end sides thereof. Each one of the motor units 15 is provided with a plurality of motors (not shown) that separately impart tensile forces to the individual wires that pass through the interiors of the flexible portions 14 and is configured so as to be driven in accordance with instructions from the control portion 6. As shown in FIG. 1, the motor units 15 are suspended at side surfaces of an operation table 16 so as to be pivotable about a horizontal axis with portions connecting with the flexible portions 14 facing vertically upward, and so as to allow position adjustment so that individual doctors (operators) can place the motor units 15 at optimal positions.

The guide tube 13 is provided with channels (not shown) that pass therethrough over the entire length thereof in the longitudinal direction, and the flexible portions 14 are inserted into the channels so as to be movable in the longitudinal directions thereof. Advancing/retracting motions of the multi-joint treatment tools 8 with respect to the bending arms are executed by manually moving the flexible portions 14 themselves in the longitudinal directions on the proximal-end side of the guide tube 13.

Figure 4:
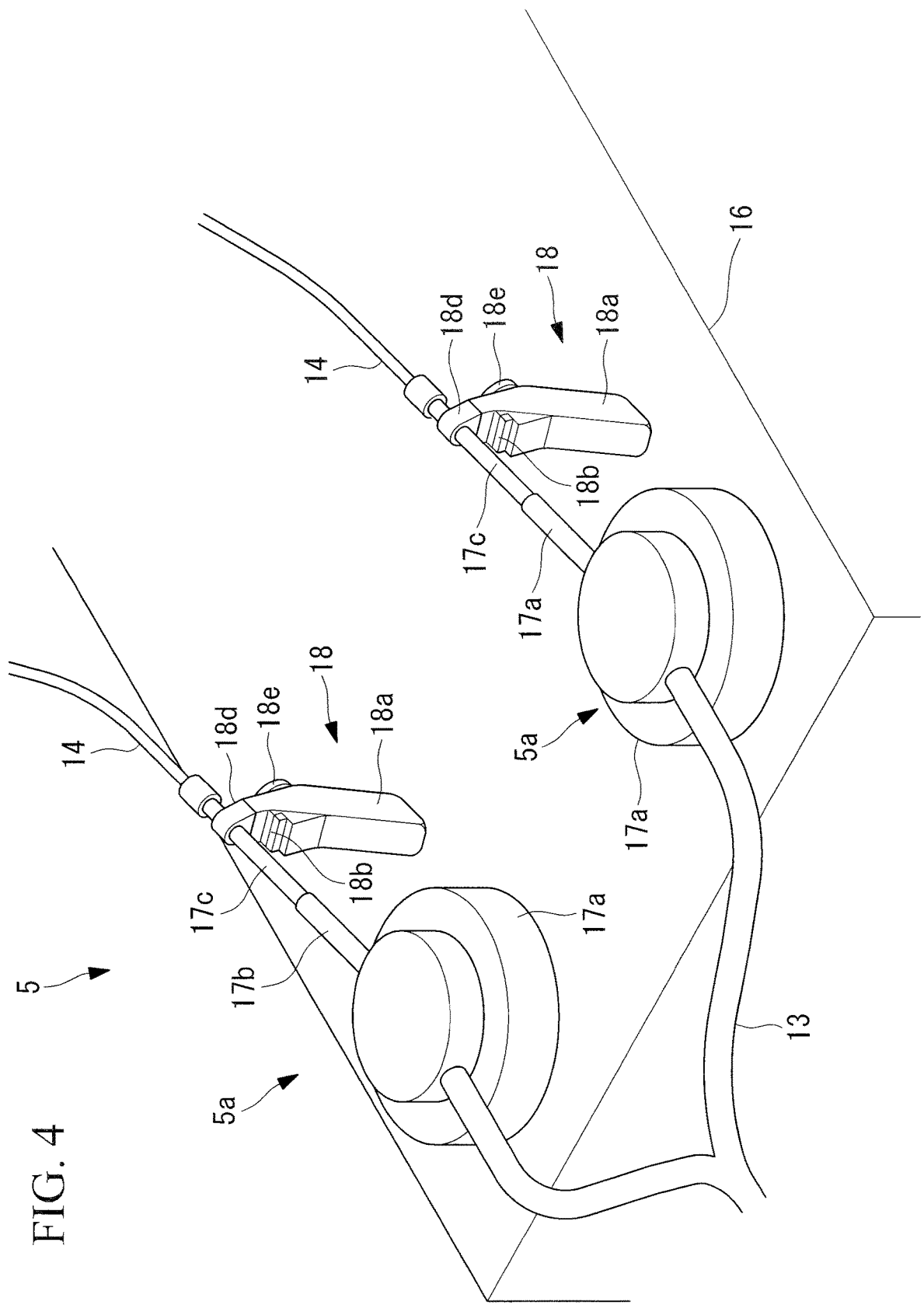
FIG. 4 is a perspective view for explaining a manipulator-operating portion provided in the surgical-manipulator system in FIG. 1.

As shown in FIGS. 1 and 4, the manipulator-operating portion 5 is provided with a pair of, that is, left and right, operating devices 5a in order for the operator to operate the manipulator-operating portion 5 with both hands. For example, the left operating device 5a is for operating the left multi-joint treatment tool 8, and the right operating device 5a is for operating the right multi-joint treatment tool 8.

Each of the operating devices 5a is provided with a manual operation portion 17 and an electric operation portion (surgical-manipulator operating device) 18.

Figure 5:
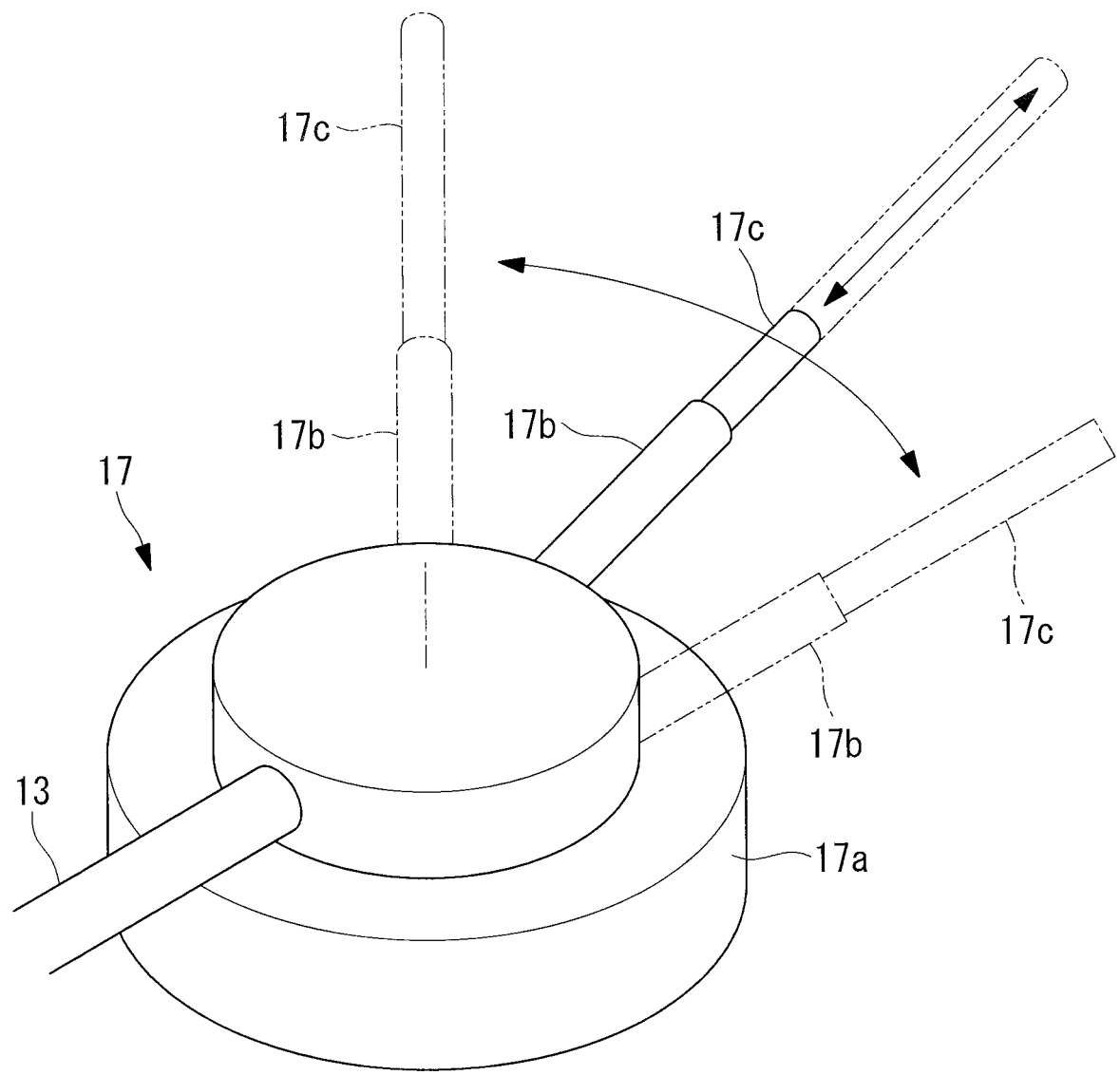
FIG. 5 is a perspective view showing a manual operation portion provided in the manipulator-operating portion in FIG. 4.

As shown in FIGS. 4 and 5, each of the manual operation portions 17 is provided with: two base portions 17a that are secured to the operation table 16 in a manner in which the positions thereof can be adjusted or in an attachable/detachable manner so that the individual doctors can place the base portions 17a at optimal positions; a cylindrical pivoting portion 17b that is supported so as to be pivotable about an axis that extends in the top-to-bottom direction with respect to the base portions 17a; and a cylindrical movable portion 17c that is disposed inside the pivoting portion 17b and that is supported so as to be movable in the longitudinal direction thereof.

The movable portions 17c are only allowed to be relatively moved in the longitudinal direction with respect to the pivoting portions 17b, and are restrained in terms of relative movement in the radial direction. By doing so, when forces are applied to the movable portions 17c in radial directions that are aligned with the pivoting directions of the pivoting portions 17b, the movable portions 17c are pivoted together with the pivoting portions 17b.

The flexible portions 14 extend so as to pass through the movable portions 17c, the pivoting portions 17b, and the base portions 17a, and are secured to the movable portions 17c in an attachable/detachable manner.

Figure 3:
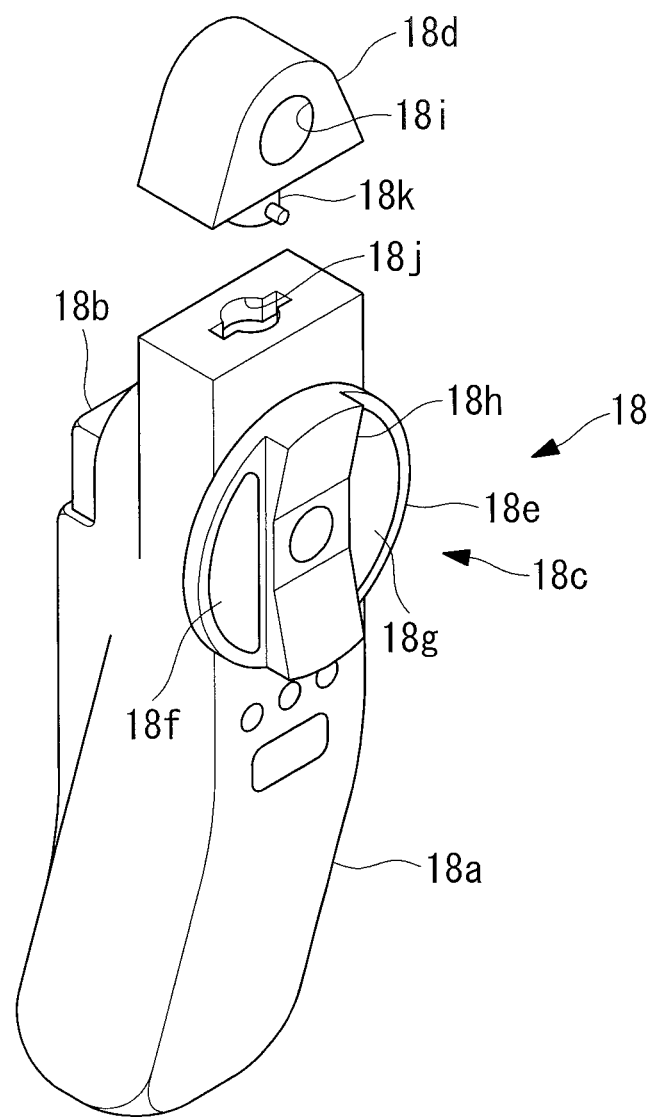
FIG. 3 is a perspective view showing a surgical-manipulator operating device according to this embodiment.

As shown in FIGS. 3 and 4, each of the electric operation portions 18 according to this embodiment is provided with: a gripping portion 18a that is gripped by the operator; a first operation input portion 18b that is operated by the index finger of the hand (for example, right hand) gripping the gripping portion 18a; a second operation input portion 18c that is similarly operated by the thumb of the gripping hand; and an attachable/detachable portion 18d for securing the electric operation portion 18 to the movable portion 17c of the manual operation portion 17 in an attachable/detachable manner.

The first operation input portions 18b are configured so as to input, for example, instruction signals for actuating the end effectors 12 at the distal ends of the multi-joint treatment tools 8. In addition, each of the second operation input portions 18c is provided with: a dial (rotating member) 18e that rotates the end effector 12 about the longitudinal axis by driving the rotational joint 8a of the multi-joint treatment tool 8; and two switches 18f and 18g that are disposed on the dial 18e and that pivot the flexing joint 8b of the multi-joint treatment tool 8.

Each of the dials 18e is formed in a discoid shape that is rotatable about an axis arranged substantially parallel to the longitudinal axis of the movable portion 17c, that is, the longitudinal axis of the flexible portion 14 that passes through the movable portion 17c, when the electric operation portion 18 is secured to the movable portion 17c. In addition, in a state in which the electric operation portion 18 is secured to the movable portion 17c, the dial 18e is disposed in a direction that faces the proximal-end side of the flexible portion 14. In other words, the dial 18e is disposed, facing the operator, at a position at which the thumb of the gripping hand would be placed when the operator grips the gripping portion 18a.

At the center of the dial 18e, a protrusion (indicator) 18h that extends in the diameter direction is provided. The protrusion 18h is disposed between the two switches 18f and 18g so as to separate them, and the operator who operates the dial 18e with his/her thumb can easily recognize the position and the direction of the protrusion 18h of the dial 18e via the tactile sensation of the thumb, and the operator can also easily recognize the positions of the two switches 18f and 18g that are disposed at positions separated by the protrusion 18h via the tactile sensation of the thumb.

In addition, the two switches 18f and 18g are provided over relatively large areas on either side of the protrusion 18h. By doing so, it is possible to correctly operate the switches 18f and 18g even if the position of the thumb of the operator who operates the switches 18f and 18g is somewhat displaced from the centers of the switches 18f and 18g.

In addition, each of the attachable/detachable portions 18d is provided with: an attaching hole 18i at which the movable portion 17c is secured after passing therethrough; and a securing protrusion 18k that secures the gripping portion 18a to the movable portion 17c in an attachable/detachable manner by being fitted to a depression 18j provided at a top end of the gripping portion 18a and by being twisted by 90° about the longitudinal axis.

Thus, as has been described above, by securing the electric operation portions 18 to the flexible portions 14 via the movable portions 17c, it is possible to operate the manual operation portions 17 by means of the electric operation portions 18 while the electric operation portions 18 that the operator touches are prevented from coming into direct contact with the flexible portions 14 in which the distal-end portions thereof are inserted into the body of a patient.

The operation of the thus-configured electric operation portions 18 and surgical-manipulator system 1 according to this embodiment will be described below.

In order to treat an affected site in the body of the patient by using the surgical-manipulator system 1 according to this embodiment, first, the inserted portion 3 of the flexible endoscope 2 in which the two multi-joint treatment tools 8 are secured in a state in which the multi-joint treatment tools 8 protrude from the distal-end surface 3a is manually introduced into the body, and the position of the distal end of the flexible endoscope 2 is adjusted so that the affected site is disposed in the viewing-field area of the flexible endoscope 2 while an image captured by using the flexible endoscope 2 is displayed on the monitor 7 and checked.

Next, while viewing an endoscope image of the area surrounding the affected site displayed on the monitor 7, the operator brings the distal ends of the multi-joint treatment tools 8 closer to the affected site. In this case, first, the operator grips the gripping portions 18a of the two electric operation portions 18 with both hands, and moves the electric operation portions 18 without operating the operation input portions 18b and 18c.

In other words, by pivoting the pivoting portions 17b with respect to the base portions 17a of the manual operation portions 17 by moving the electric operation portions 18 left and right, the bending arms of the moving mechanism 10 secured at the distal end of the inserted portion 3 are pivoted in corresponding directions, and thus, the multi-joint treatment tools 8 as a whole are moved left and right. In addition, the multi-joint treatment tools 8 as a whole are advanced and retracted by advancing and retracting the movable portions 17c with respect to the pivoting portions 17b of the manual operation portions 17 by moving the electric operation portions 18 forward and backward.

By doing so, because the positions of the distal ends of the multi-joint treatment tools 8 are roughly set with respect to the affected site, in this state, the operator operates the second operation input portions 18c provided in the electric operation portions 18, thus performing precise positioning with respect to the affected site by electrically driving the rotational joints 8*a* and the flexing joints 8*b* of the individual multi-joint treatment tools 8, and actuates the end effectors 12 by operating the first operation input portions 18*b*. Accordingly, the affected site can be treated.

In this case, with the electric operation portion 18 according to this embodiment, for example, as shown in FIG. 3, when the dial 18*e* attached to the gripping portion 18*a* is disposed at a rotational position at which the protrusion 18*h* is disposed in a top-to-bottom direction, the two switches 18*f* and 18*g* on the dial 18*e* are disposed left and right of the protrusion 18*h*. Therefore, by pressing one of the switches 18*f* and 18*g*, as shown in FIG. 2, it is possible to pivot the end effector 12 in the left-to-right direction by means of the flexing joint 8*b*.

When starting the operation, it is desirable to perform initialization in which the positional relationship of the switches 18*f* and 18*g* is aligned with the pivoting direction of the flexing joint 8*b* of the multi-joint treatment tool 8 appearing on the endoscope screen. In an initial state, initializing motions may be performed so that the directions of the multi-joint treatment tool 8 and the switches 18*f* and 18*g* of the electric operation portion 18 become the same. In addition, in a state in which, before starting the operation, the linkage (master-slave connection) between the electric operation portion 18 and the multi-joint treatment tool 8 is disabled, the master and the slave may be connected by using a clutch switch (not shown) after the operator himself/herself has rotated the dial 18*e* to align the directions. The alignment of the directions may also be maintained by the same method in the case in which the direction of the switches 18*f* and 18*g* and the direction of the multi-joint treatment tool 8 are displaced during operation.

Figure 6:
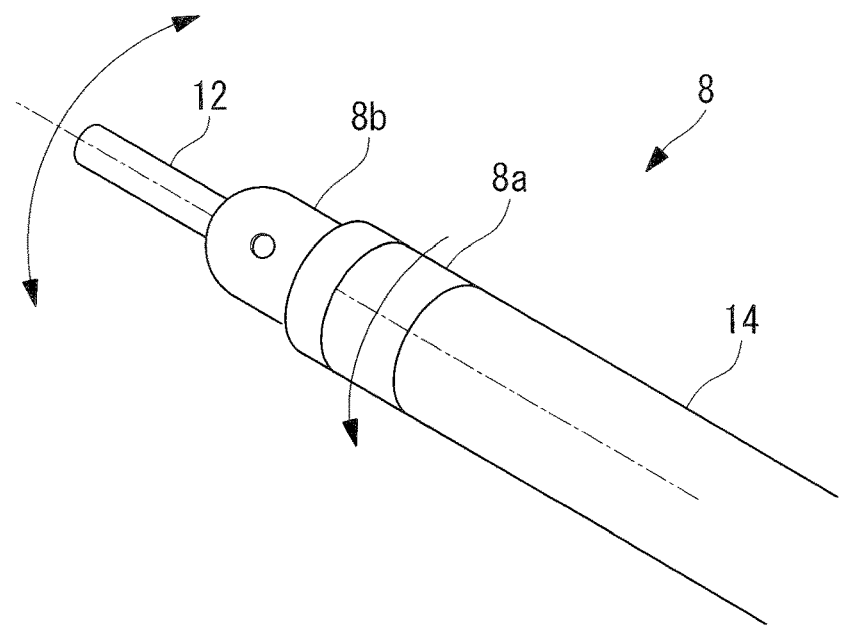
FIG. 6 is a perspective view showing a state in which the pivoting direction of an end effector is rotated by a rotational joint of the surgical manipulator in FIG. 2.
Figure 7:
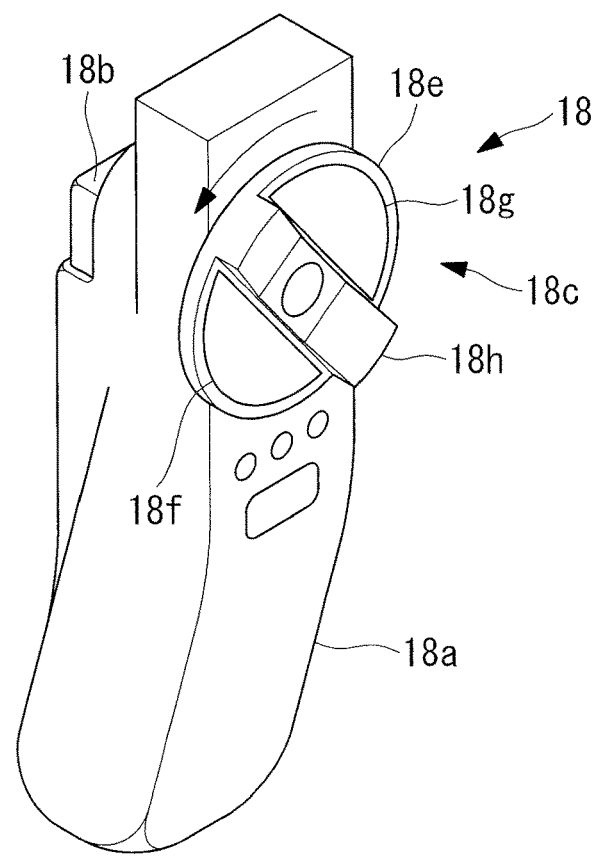
FIG. 7 is a perspective view for explaining the operation of the surgical-manipulator operating device in FIG. 3 for performing the motion in FIG. 6.

On the other hand, when the dial 18*e* is rotated as shown in FIG. 7, the rotational joint 8*a* is rotated as shown in FIG. 6, and, consequently, the flexing direction of the flexing joint 8*b* disposed on the distal-end side of the rotational joint 8*a* is changed in a diagonally left-to-right direction. In this case, with this embodiment, because the two switches 18*f* and 18*g* are provided on the dial 18*e*, when the dial 18*e* is rotated as shown in FIG. 7, the switches 18*f* and 18*g* are also rotated and the arrangement direction thereof is also changed in a diagonally left-to-right direction.

In other words, from the perspective of the operator, the rotating direction of the rotational joint 8*a* of the multi-joint treatment tool 8 in the endoscope image displayed on the monitor 7 is aligned with the rotating direction of the dial 18*e* of the electric operation portion 18 he/she is gripping, and the pivoting direction of the end effector 12 due to the flexing joint 8*b* is also aligned with the direction in which the switches 18*f* and 18*g* are arranged on the dial 18*e*. Therefore, the operator can intuitively understand the directions in which the dial 18*e* and switches 18*f* and 18*g* should be operated in order to pivot the end effector 12 in a desired direction, and thus, there is an advantage in that, even if the dial 18*e* is rotated to actuate the rotational joint. 8*a*, it is possible to input appropriate flexion instructions for flexing the flexing joint 18*b* without causing confusion.

In addition, with this embodiment, because the protrusion 18*h* is provided on the dial 18*e*, the operator can check the rotational angle of the dial 18*e* on the basis of the position of the protrusion 18*h* on the dial 18*e*. In addition, because the switches 18*f* and 18*g* are provided on either side of the protrusion 18*h*, the operator can easily check the positions of the switches 18*f* and 18*g* with reference to the protrusion 18*h*.

In particular, because the rotational angle of the dial 18*e* can be checked by using the indicator that can be checked via the tactile sensation, as with the protrusion 18*h*, just by checking the direction of the protrusion 18*h* via the tactile sensation of the thumb, it is also possible to check the arrangement direction of the switches 18*f* and 18*g* that are on either side thereof, and thus, it is possible to pivot the end effector 12 in the correct direction on the basis of the feeling of hands without looking away from the monitor 7. Accordingly, the operator can perform an operation in a state in which the operating field (the end effector 12 to be operated and a target tissue) is always in sight, and thus, it is possible to decrease the surgery time by enhancing the operation efficiency.

Because the operating field is always kept in sight, it is possible to prevent the end effector 12 from being unintentionally brought close to the tissue. In addition, because the switches 18*f* and 18*g* are formed in relatively large sizes, it is possible to reliably operate the switches 18*f* and 18*g* even if the thumb of the operator is displaced from the centers of the switches 18*f* and 18*g*. It is also possible to achieve the same function by employing a depression like a groove instead of the protrusion 18*h*.

Figure 8:
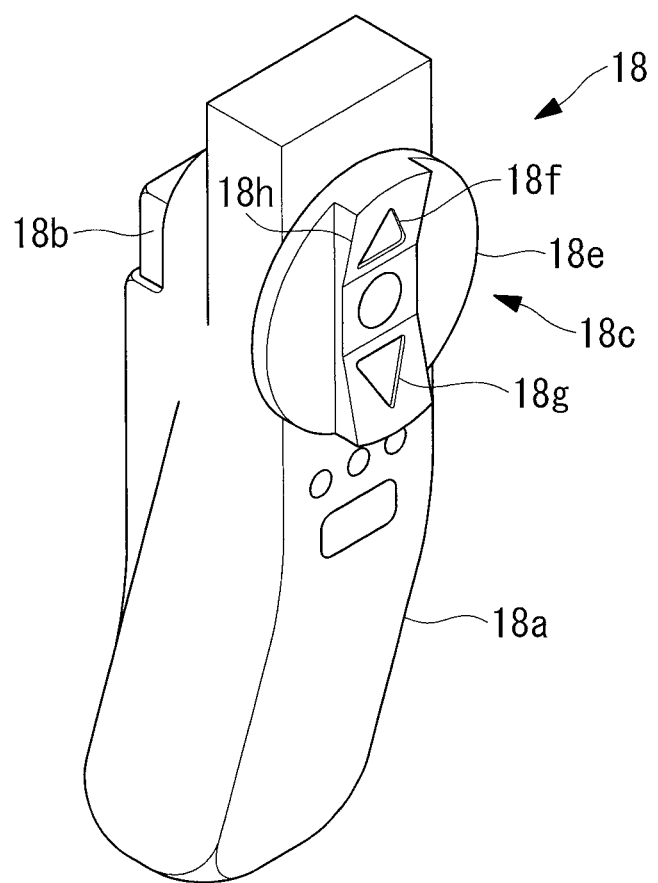
FIG. 8 is a perspective view showing a first modification of the surgical-manipulator operating device in FIG. 3.

Note that, with this embodiment, although the switches 18*f* and 18*g* are provided on either side of the protrusion 18*h*, alternatively, the switches 18*f* and 18*g* may be disposed on the protrusion 18*h*, as shown in FIG. 8. In this case, because the direction in which the protrusion 18*h* extends is aligned with the direction in which the switches 18*f* and 18*g* are arranged, the dial 18*e* may be rotated so that the direction in which the protrusion 18*h* extends becomes aligned with the pivoting direction of the end effector 12.

Figure 9:
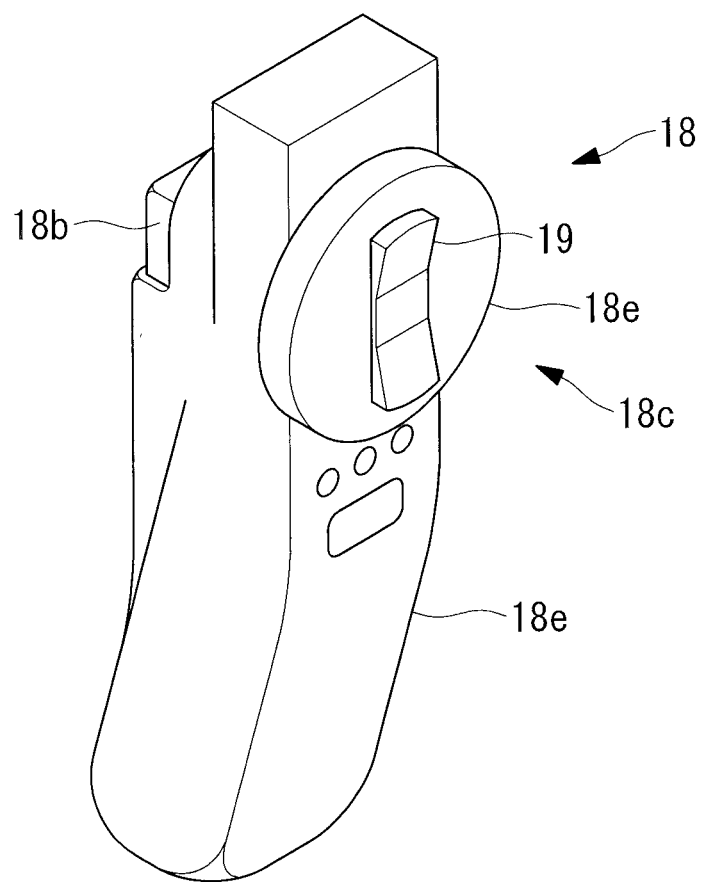
FIG. 9 is a perspective view showing a second modification of the surgical-manipulator operating device in FIG. 3.

In addition, as shown in FIG. 9, a switch 19 itself, which is provided in the dial 18*e*, may be utilized as a protrusion.

Figure 10A:
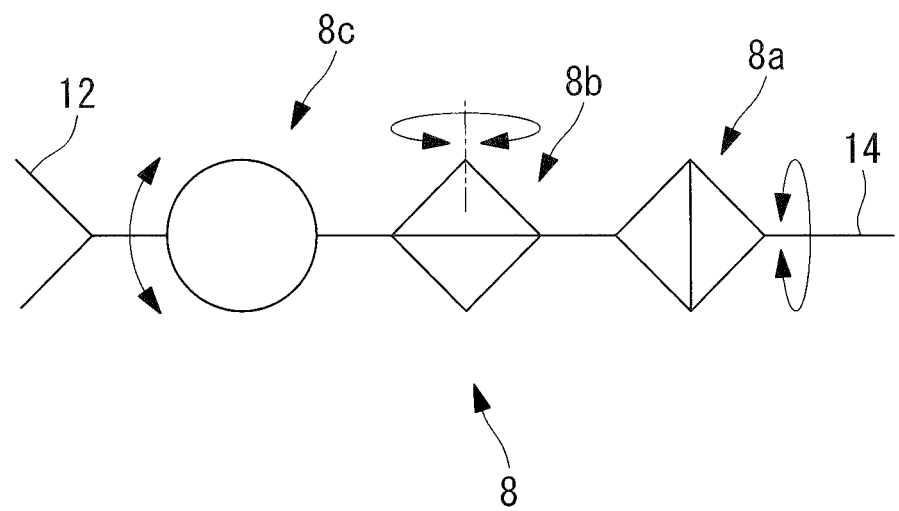
FIG. 10A is a diagram showing, in outline, another axial configuration of the surgical manipulator.
Figure 10B:
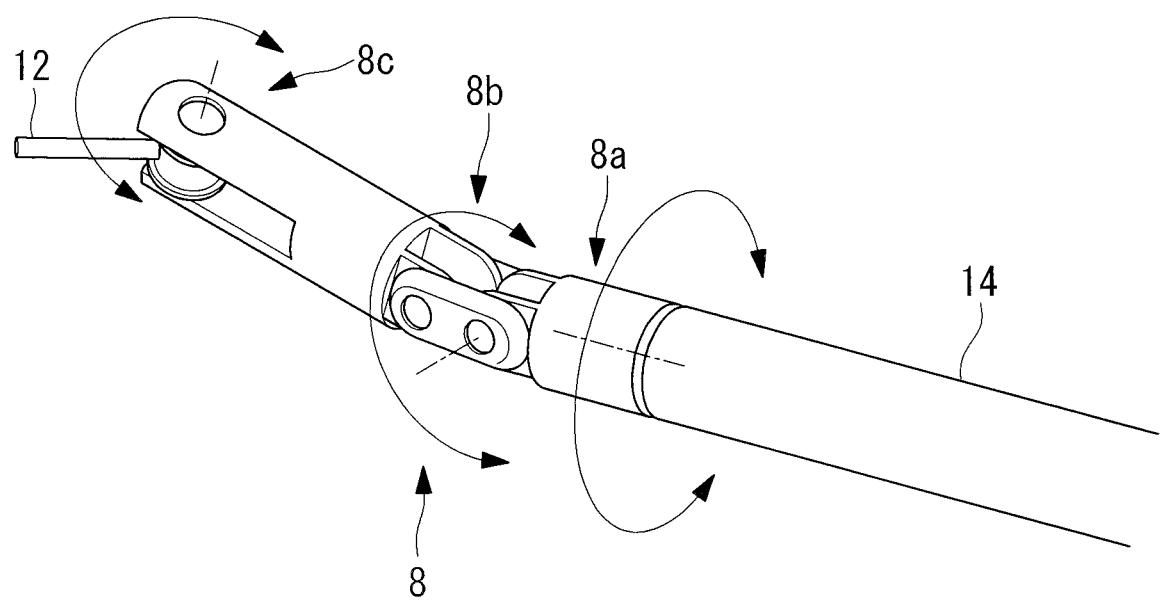
FIG. 10B is a perspective view showing another axial configuration of the surgical manipulator.

In addition, as the axial configuration of the multi-joint treatment tool 8, as shown in FIGS. 10A and B, two or more flexing joints 8*b* and 8*c* may be arranged in series on the distal-end side of the rotational joint 8*a*. In the example illustrated in FIGS. 10A and B, two flexing joints 8*b* and 8*c*, which flex in directions that are orthogonal to each other, are provided.

Figure 11:
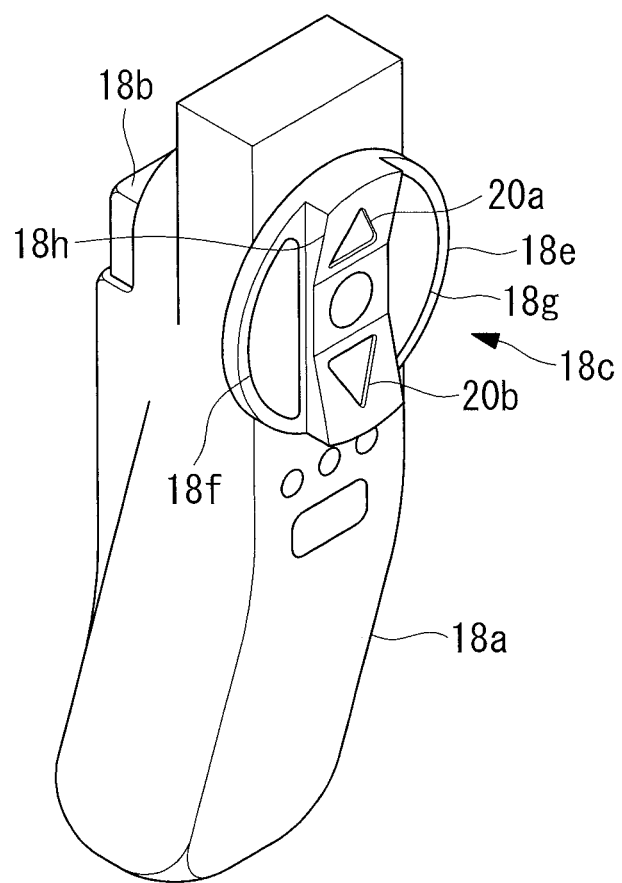
FIG. 11 is a perspective view showing a third modification of the surgical-manipulator operating device in FIG. 3 for operating the surgical manipulator in FIG. 10.

Also, in this case, two sets of switches 18*f* and 18*g* and 20*a* and 20*b* for separately operating the flexing joints 8*b* and 8*c*, which work in two directions that are orthogonal to each other, may be arranged on the dial 18*e* of the electric operation portion 18, as shown in FIG. 11. In the example illustrated in FIG. 11, it is possible to separately operate the flexing joints 8*b* and 8*c*, whose flexing directions are orthogonal to each other, by using one set of the switches 18*f* and 18*g* that are disposed on either side of the protrusion 18*h* and another set of the switches 20*a* and 20*b* that are arranged in the direction in which the protrusion 18*h* extends.

Figure 12:
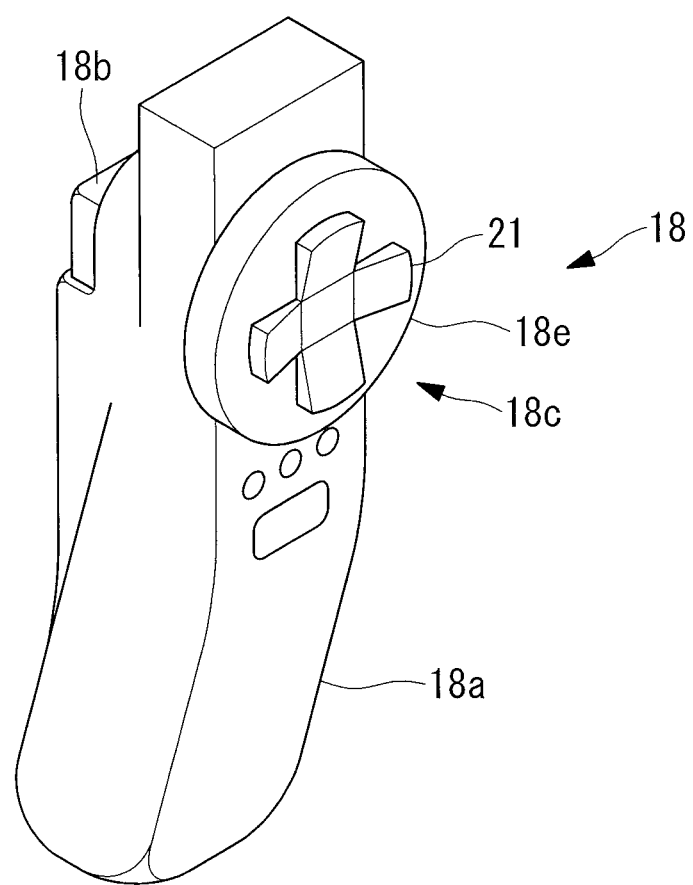
FIG. 12 is a perspective view showing a fourth modification of the surgical-manipulator operating device in FIG. 3 for operating the surgical manipulator in FIG. 10.

In addition, in the example illustrated in FIG. 12, a switch 21 itself, which is disposed on the dial 18*e*, is constituted of a cross key, and flexion instructions for two orthogonal directions are input by using the switch 21 constituted of the cross key. In addition, the switch 21 constituted of the cross key serves as an indicator with which the direction of the dial 18*e* can be checked via the tactile sensation.

Figure 13:
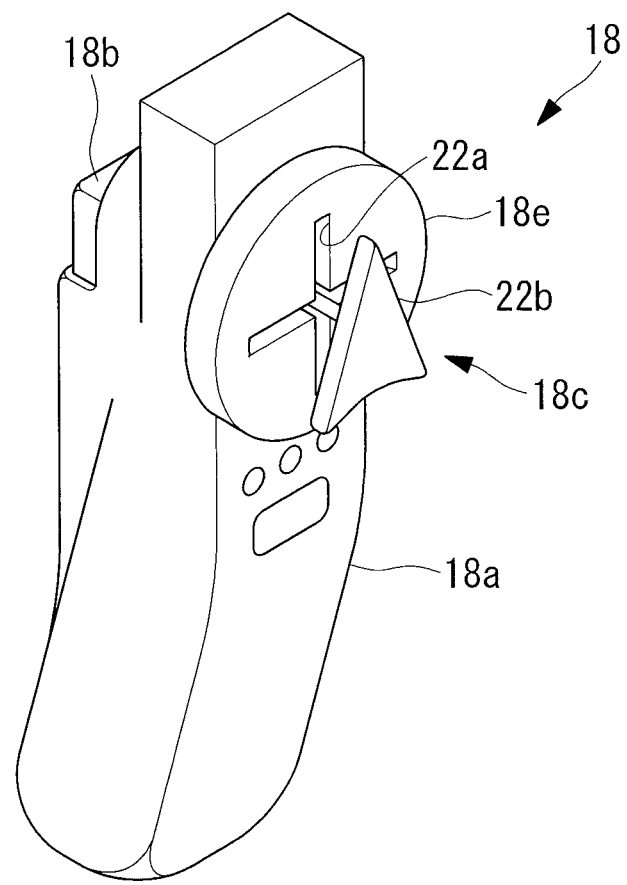
FIG. 13 is a perspective view showing a fifth modification of the surgical-manipulator operating device in FIG. 3 for operating the surgical manipulator in FIG. 10.

In addition, the example illustrated in FIG. 13 is provided with a joystick-style switch 22*b* that can be pivoted in two directions along a cross-shaped groove 22*a* provided on the dial 18*e*. By doing so also, it is possible to input, even if the dial 18*e* is rotated to actuate the rotational joint 8*a*, appropriate flexion instructions for separately flexing the two flexing joints 8*b* and 8*c* without causing confusion.

In addition, with this embodiment, although the switches 18*f* and 18*g* that rotate together with the dial 18*e* are provided on the dial 18*e*, alternatively, the same function may be achieved without providing the switches on the dial 18*e*. In the example illustrated in FIG. 14, only the protrusion 18*h* is provided on the dial 18*e*.

The dial 18*e* is configured so that it is possible to selectively press given circumferential-direction positions in the vicinity of outer circumference thereof, and sensors 23*a* to 23*d* that detect the pressed circumferential-direction positions (operating positions) in the dial 18*e* are disposed on the back side of the dial 18*e* on the gripping portion 18*a* side. Also a signal generating portion (not shown), which generates and outputs flexion instructions for the flexing joints 8*b* and 8*c* on the basis of the rotational angle of the dial 18*e* and the operating positions detected by the sensors 23*a* to 23*d*, may be provided.

To be more specific, the four sensors 23*a* to 23*d* are disposed at the top, bottom, left, and right around the center of the dial 18*e*, as shown in FIG. 15, so as to detect a pressed position among the circumferential directions of the dial 18*e*. A V-groove 24 at the outermost circumference in FIG. 15 indicates, for example, the top-end position of the protrusion 18*h* in the dial 18*e* in FIG. 14.

Figure 14:
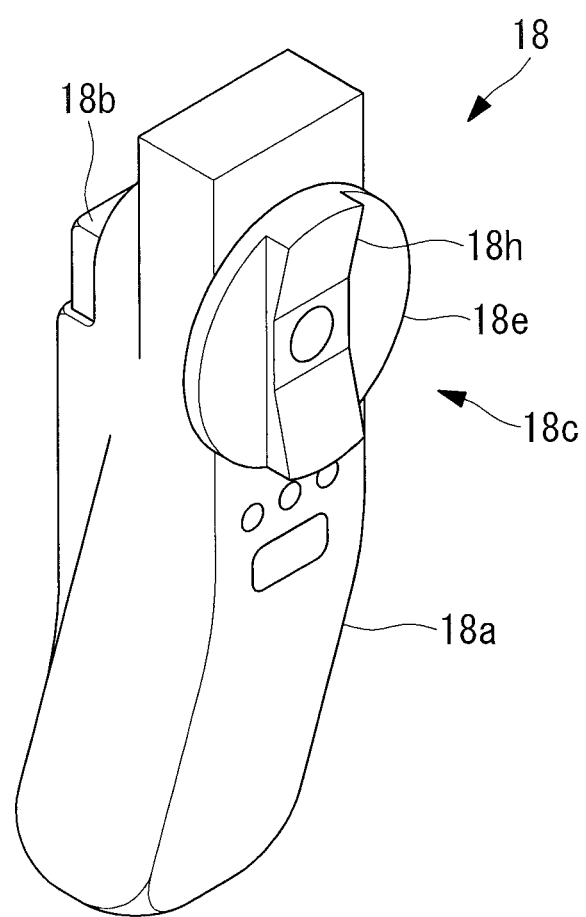
FIG. 14 is a perspective view showing a sixth modification of the surgical-manipulator operating device in FIG. 3.
Figure 15A:
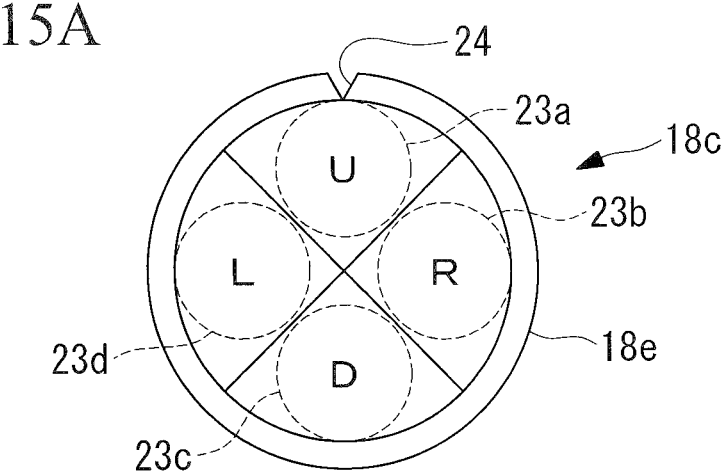
FIG. 15A is a schematic diagram for explaining the operation of the surgical-manipulator operating device in FIG. 14.
Figure 15B:
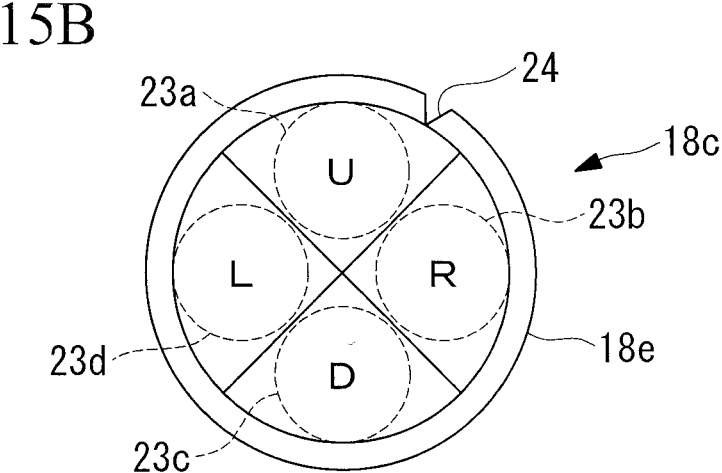
FIG. 15B is a schematic diagram for explaining the operation of the surgical-manipulator operating device in FIG. 14.

In the case in which the protrusion 18*h* is placed in a range of ±45°, that is, a total of 90°, centered on the position in FIG. 14, the signal generating portion generates and outputs, as shown in FIGS. 15A and B, flexion instructions for pivoting the end effector 12 to the upper side (U) when the upper side of the dial 18*e* is pressed, flexion instructions for pivoting the end effector 12 to the down side (D) when the bottom side of the dial 18*e* is pressed, flexion instructions for pivoting the end effector 12 to the left side (L) when the left side of the dial 18*e* is pressed, and flexion instructions for pivoting the end effector 12 to right side (R) when the right side of the dial 18*e* is pressed.

Figure 15C:
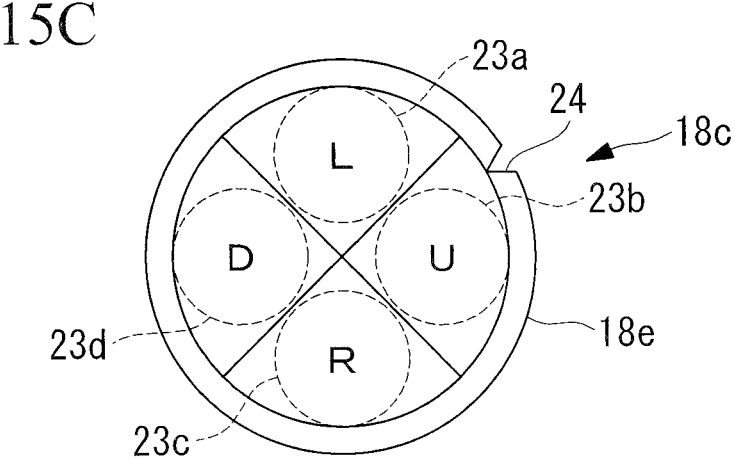
FIG. 15C is a schematic diagram for explaining the operation of the surgical-manipulator operating device in FIG. 14.
Figure 15D:
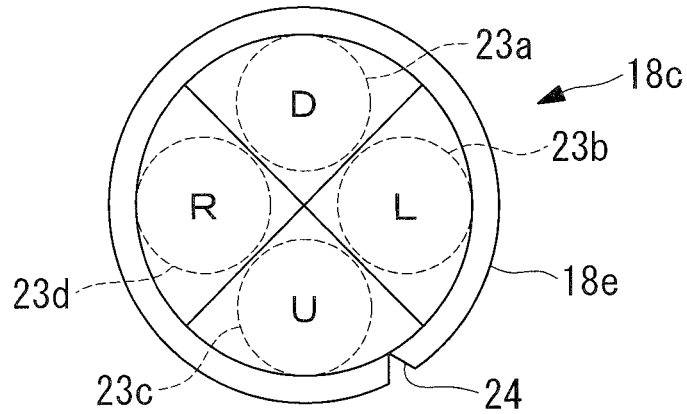
FIG. 15D is a schematic diagram for explaining the operation of the surgical-manipulator operating device in FIG. 14.

Then, in the case in which the dial 18*e* is further rotated, and the protrusion 18*h* is moved beyond the above-described 90°-range, as shown in FIG. 15C, the flexion instructions generated by the signal generating portion are changed. In other words, when the position of the V-groove 24 at the outermost circumference is pressed, the flexion instructions for pivoting the end effector 12 to the upper side (U) are generated and output. In the case in which the dial 18*e* is further rotated, and the protrusion 18*h* is moved beyond the next 90°-range also, as shown in FIG. 15D, when the position of the V-groove 24 at the outermost circumference is pressed, the signal generating portion generates and outputs the flexion instructions for pivoting the end effector 12 to the upper side (U).

By doing so also, regardless of the rotational position of the dial 18*e*, it is possible to always generate the flexion instructions for pivoting the end effector 12 to the upper side (U) when the position of the V-groove 24 is pressed. Therefore, because it is not necessary to dispose the switches 18*f* and 18*g* on the rotating dial 18*e*, it is possible to simplify the wiring for the sensors 23*a* to 23*d*.

In addition, in the example illustrated in FIG. 15, although the flexion instructions to be generated when the same sensors among the sensors 23*a* to 23*d* detect the operating positions are changed every time the dial 18*e* is rotated by a rotational angle of 90°, alternatively, in the case in which simultaneous detection by two of the sensors 23*a* to 23*d* is allowed, as shown in FIG. 16, the flexion instructions to be generated when the same sensors among the sensors 23*a* to 23*d* detect the operating positions may be changed every time the dial 18*e* is rotated by a rotational angle of 45°.

Figure 16A:
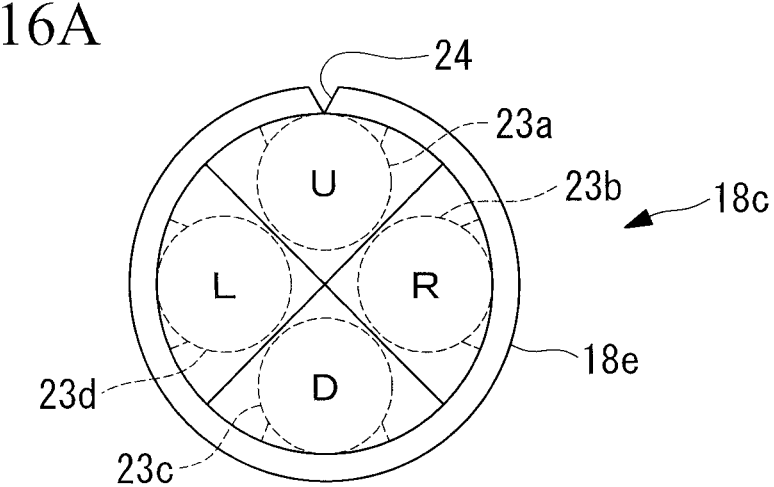
FIG. 16A is another schematic diagram for explaining the operation of the surgical-manipulator operating device in FIG. 14.
Figure 16B:
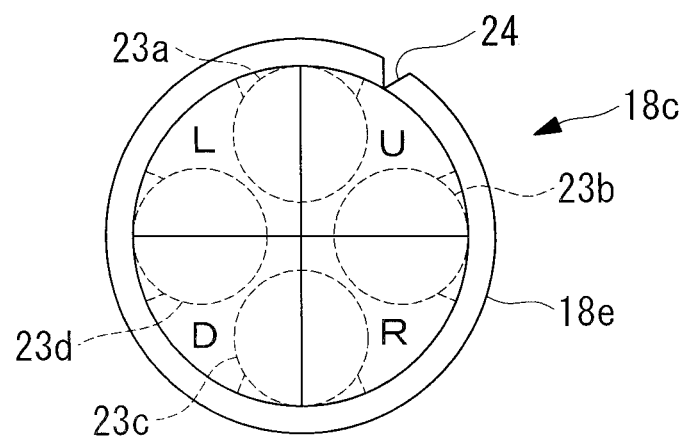
FIG. 16B is another schematic diagram for explaining the operation of the surgical-manipulator operating device in FIG. 14.
Figure 16C:
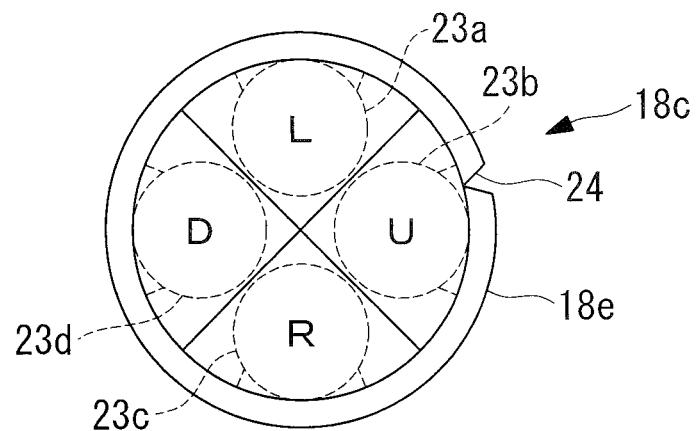
FIG. 16C is another schematic diagram for explaining the operation of the surgical-manipulator operating device in FIG. 14.
Figure 16D:
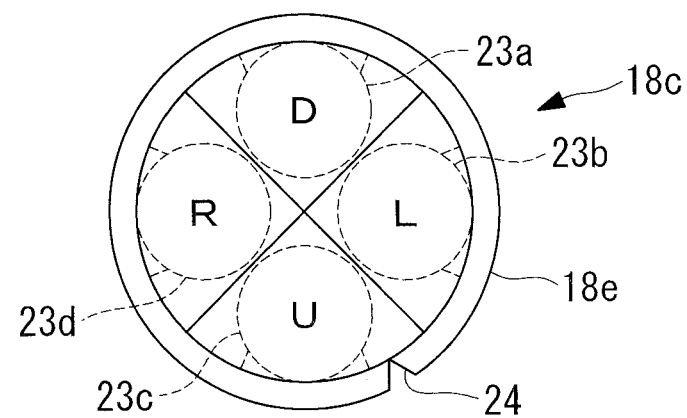
FIG. 16D is another schematic diagram for explaining the operation of the surgical-manipulator operating device in FIG. 14.

Specifically, in the case in which the protrusion 18*h* is placed in a range of ±22.5°, that is, a total of 45°, centered on the position in FIG. 14, starting from the state in which the signal generating portion generates and outputs the flexion instructions for pivoting the end effector 12 to the upper side (U) when the upper side of the dial 18*e* is pressed, as shown in FIG. 16A, the flexion instructions to be generated by the signal generating portion may be changed every time the dial 18*e* is rotated by 45° beyond the above-described 45°-range, as shown in FIG. 16B to D.

Without limitation to the above-described configuration, it is possible to realize the detection sensors by the same method regardless of the angular resolution. For example, in the case in which a detection sensor can continuously acquire all positional information of circumferential directions, as with a touch screen sensor, the detection sensor can be realized by moving the mapping relationship between the sensor and output by the amount by which the dial 18*e* is rotated.

Figure 17A:
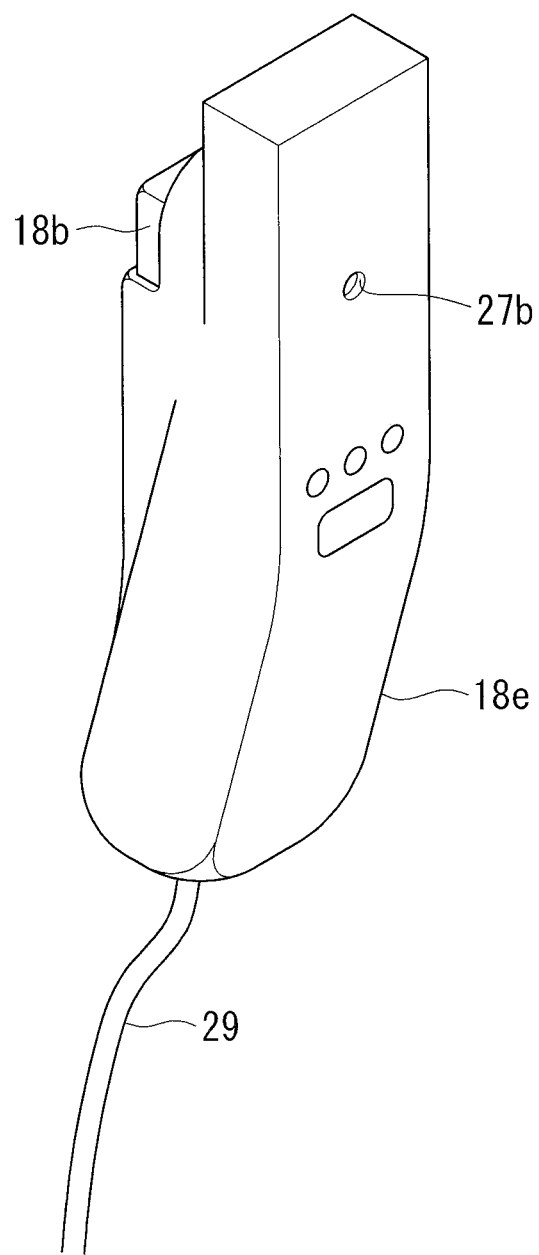
FIG. 17A is a perspective view showing a seventh modification of the surgical-manipulator operating device in FIG. 3 and a portion thereof to be reused.
Figure 17B:
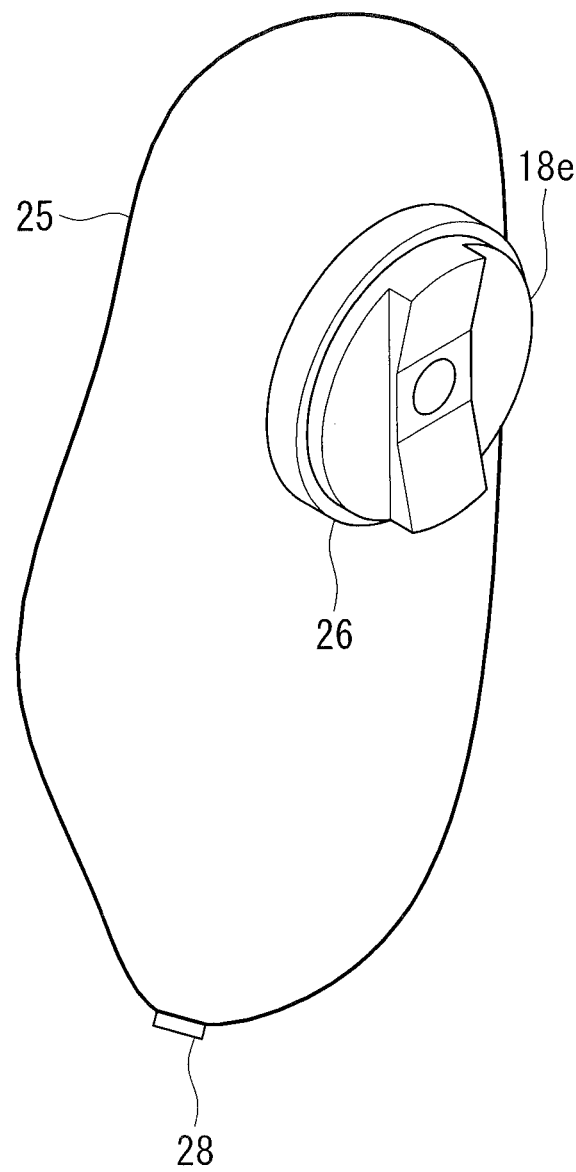
FIG. 17B is a perspective view showing the seventh modification of the surgical-manipulator operating device in FIG. 3 and a drape thereof.
Figure 18:
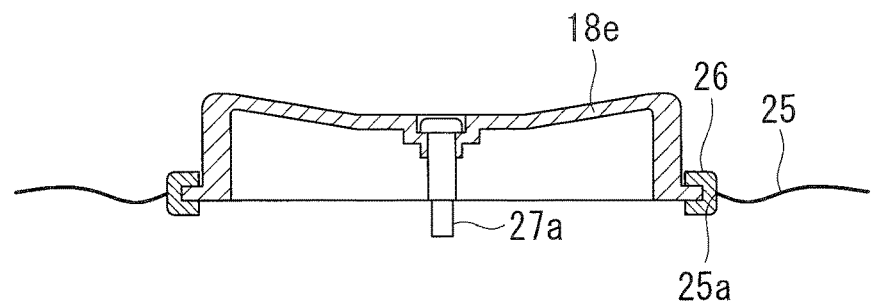
FIG. 18 is a longitudinal cross-sectional diagram showing a dial attached to the drape in FIG. 17.
Figure 19:
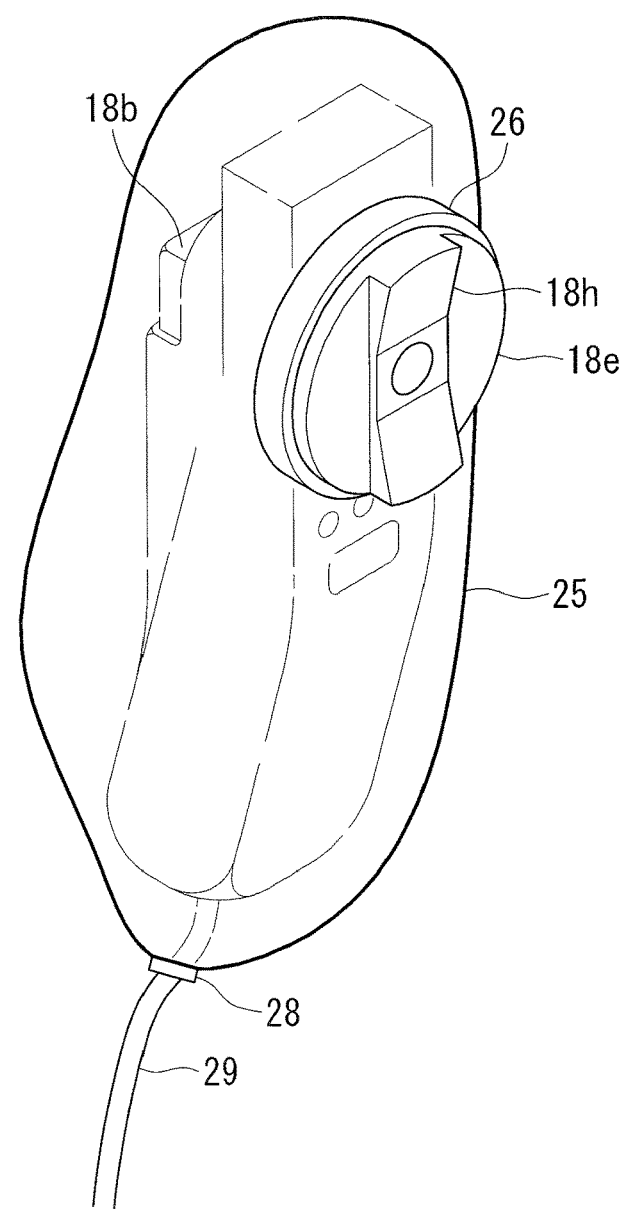
FIG. 19 is a perspective view showing the surgical-manipulator operating device in a state in which the device is covered by the drape in FIG. 17.

In addition, as shown in FIGS. 17 to 19, by covering the electric operation portion 18 with a drape 25, it is possible to reuse the electric operation portion 18. Because the electric operation portion 18 includes sensors such as the switches 18*f* and 18*g* or the like, it is difficult to employ a sterilization method that uses high-temperature vapor. Because of this, it is preferable that the electric operation portion 18 be covered with the drape 25 that has been sterilized before operation, and that the electric operation portion 18 be reused by disposing the drape 25 after completing all operations. In this case, because it would be difficult to operate the dial 18*e* if the drape 25 covers the dial 18*e* together with the electric operation portion 18, as shown in FIG. 17, the dial 18*e* that can be attached to and detached from the gripping portion 18*a* may be provided on the drape 25 side.

Specifically, as shown in FIG. 18, a through-hole 25*a* may be provided in a portion of the drape 25, a ring-like seal member 26 may be placed in the through-hole 25*a*, and the dial 18*e* may be fitted to the seal member 26 in a rotatable manner. By doing so, starting from a separated state, as shown in FIGS. 17A and B, the gripping portion 18*a* shown in FIG. 17A is covered with the drape 25 shown in FIG. 17B, an attaching shaft 27*a* of the dial 18*e* on the drape 25 side is fitted to a fitting hole 27*b* of the gripping portion 18*a*, and thus, the entire gripping portion 18*a* can be covered with the drape 25, with only the dial 18*e* exposed, as shown in FIG. 19. In FIG. 19, the reference sign 28 is a stopper ring (stretching rubber) that closes a hole through which a cable 29 to be connected to the gripping portion 18*a* passes. The stopper ring 28 may be stretched, the entire gripping portion 18*a* may be placed in that stopper ring 28 to cover the gripping portion 18*a* with the drape 25, and then, the dial 18*e* may be attached.

Figure 20:
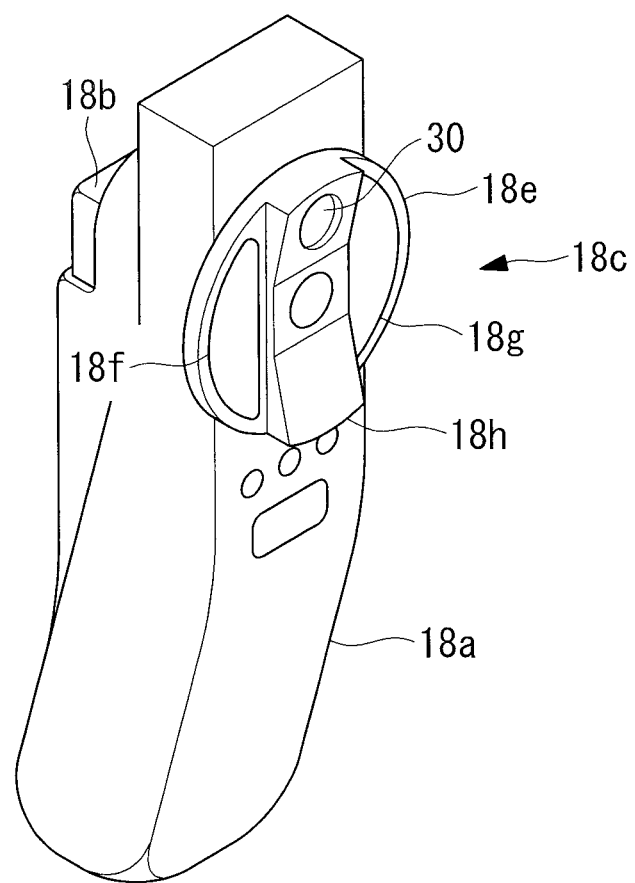
FIG. 20 is a perspective view showing an eighth modification of the surgical-manipulator operating device in FIG. 3.

In addition, in this embodiment, an operation key 30 for actuating the end effector 12 may be provided in the dial 18*e*, as shown in FIG. 20. In the example illustrated in FIG. 20, the operation key 30 is provided in the protrusion 18*h*. By doing so, the operator can check, with reference to the protrusion 18*h*, the rotational angle of the dial 18*e*, as well as positions of the switches 18*f* and 18*g* and the operation key 30, via the tactile sensation without having to look at the dial 18*e*.

The operation key 30 may be used for aligning attitudes when the attitude of the multi-joint treatment tool 8 and the directions of the switches 18*f* and 18*g* of the electric operation portion 18 are displaced. In addition, the operation key 30 can also be utilized, by the same method, for performing the initializing motions when starting operation. In this way, by providing the operation key 30 at a position that is checked via the tactile sensation, it is possible to easily switch to the attitude aligning mode during operation for inputting rotation and inputting flexion via the dial 18e and the switches 18f and 18g without looking away from the monitor 7.

In addition, in the case in which the end effector 12 is a treatment tool that utilizes a high-frequency power source, the operation key 30 may be used as a switch for powering the high-frequency treatment tool. In this case also, it is possible to seamlessly perform the operation of the joints 8a and 8b of the multi-joint treatment tool 8 and the operation for powering the high-frequency treatment tool.

In addition, in this embodiment, the dial 18e for the operator to operate the multi-joint treatment tool 8 may be utilized for another operation.

Figure 21:
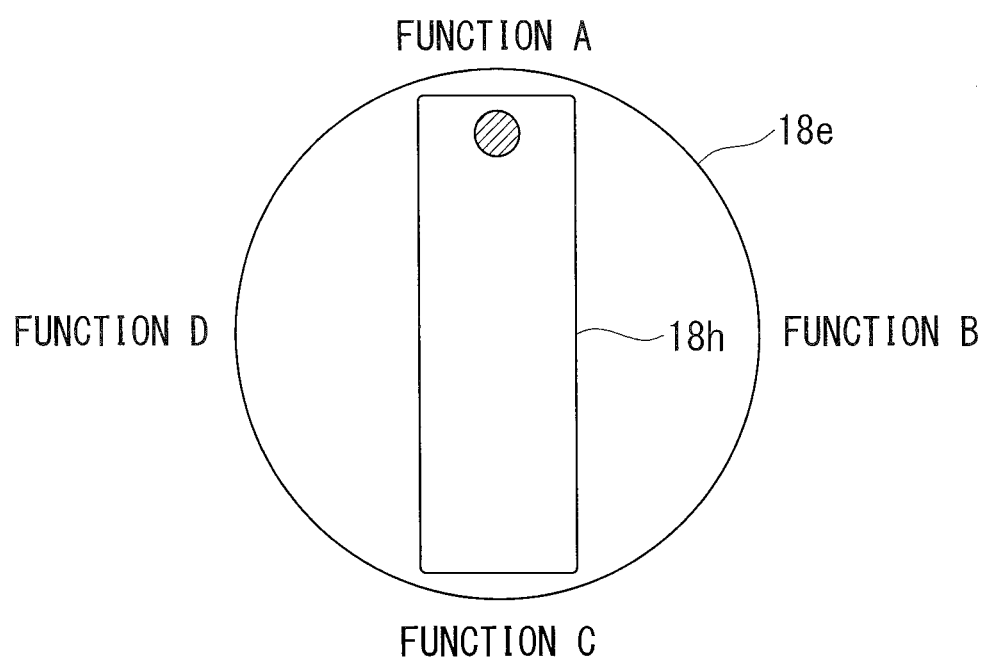
FIG. 21 is a diagram showing an example of utilizing the dial for another usage.
Figure 22:
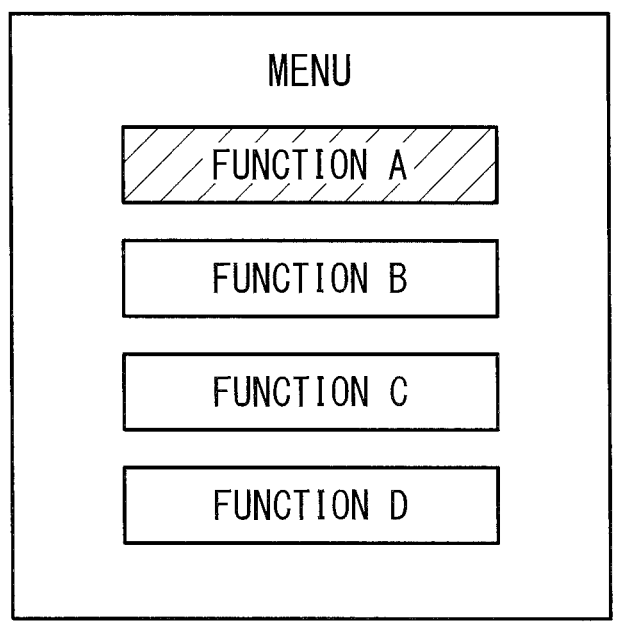
FIG. 22 is a diagram showing an example of a menu screen corresponding to FIG. 21.

For example, another mode may be prepared in addition to a operation mode for operating the multi-joint treatment tool 8, and in the case in which this other mode is selected, the dial 18e may be used as a selection dial for selecting functions A to D, as shown in FIG. 21. Also, the function selection may be confirmed when a switch on the dial 18e or a circumferential-direction portion of the dial 18e is pressed. FIG. 22 shows an example of a menu display when another mode is selected.

In addition, by providing a limit sensor 31 that detects a predetermined rotational angle of the dial 18e, displacement between the rotational angle of the dial 18e and the rotational angle of the rotational joint 8a may be corrected by using the detection results from the limit sensor 31.

Figure 23A:
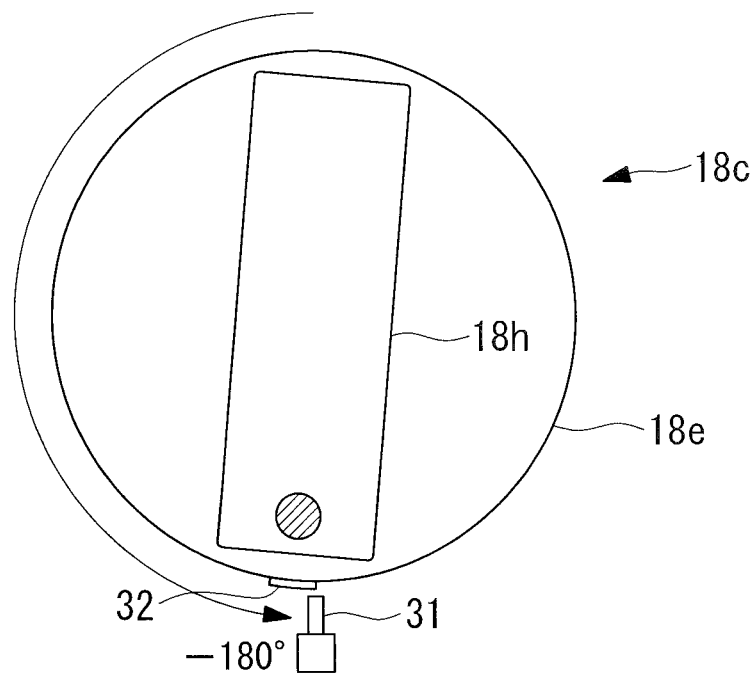
FIG. 23A is a diagram for explaining a limit sensor that detects the two ends of a range of dial rotational angles.
Figure 23B:
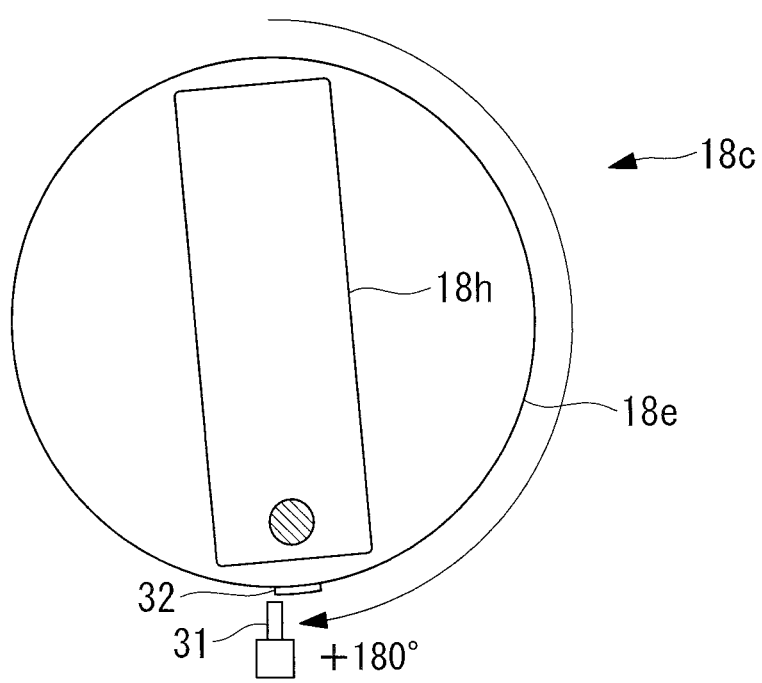
FIG. 23B is a diagram for explaining the limit sensor that detects the two ends of the range of the dial rotational angles.

For example, in the example illustrated in FIG. 23, ±180° at two ends of the rotational angle range of the dial 18e are detected by the limit sensor 31. In the figure, the reference sign 32 is a dog for detection.

Figure 24:
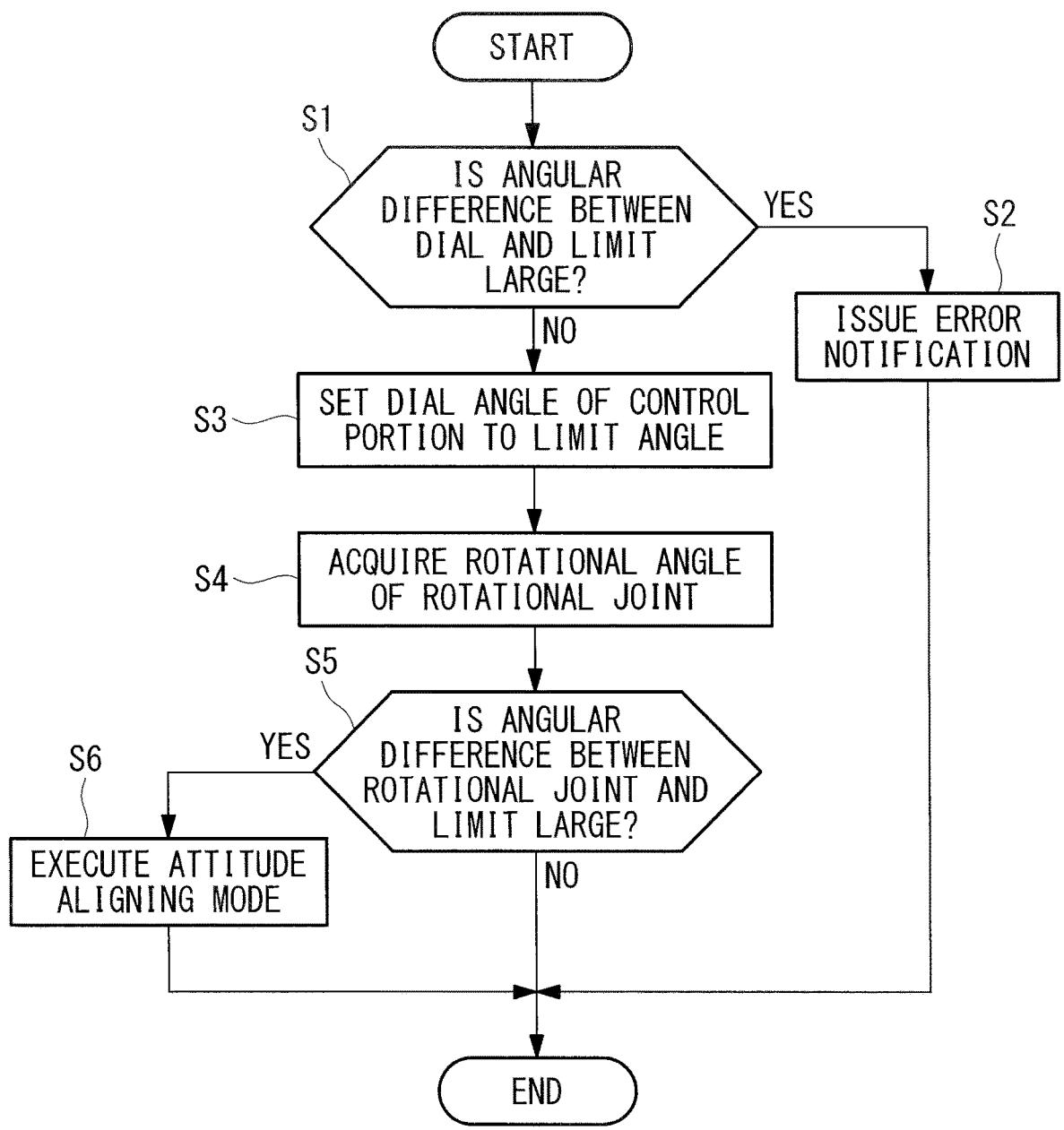
FIG. 24 is a flowchart showing an angle correction method employing the limit sensor in FIG. 23.

As a method of correcting the rotational angle displacement, for example, when the limit sensor 31 detects +180°, as shown in FIG. 24, the angle is compared with the current angle of the dial 18e retained by the control portion 6 (step S1), and, in the case in which the angular difference is greater than a predetermined threshold, an alarm is issued to notify the presence of an abnormality in a rotation sensor (not shown) in the electric operation portion 18 or the limit sensor 31 (step S2). On the other hand, in the case in which the angular difference is less than the threshold, the current angle of the dial 18e retained by the control portion 6 is updated to +180° (step S3).

Next, the angle of the rotational joint 8a of the multi-joint treatment tool 8 is acquired (step S4), the acquired angle of the rotational joint 8a is compared with +180° (step S5), the attitude aligning mode is executed in the case in which the angular difference is greater than the predetermined threshold (step S6), and the operation is continued in the case in which the angular difference is less than the threshold.

The following method is conceivable as a method of, in the attitude aligning mode, aligning the rotational angle of the dial 18e with the angle of the rotational joint 8a of the multi-joint treatment tool 8.

Example methods include one in which, in the case in which the angle of the rotational joint 8a is +160° when the limit sensor 31 has detected +180°, the rotational joint 8a is not moved until the dial 18e is rotated and the rotational angle of the dial 18e reaches +160°, and the rotational joint 8a is rotated in accordance with the rotation angle of the dial 18e when +160° is reached.

In addition, for example, within a predetermined motion range (for example, from +180° to +110°) of the dial 18e, the rotational joint 8a may be moved by decreasing the ratio (motion-scale ratio) of the rotation angle of the rotational joint 8a with respect to the rotation angle of the dial 18e, and the rotational joint 8a may be moved by restoring the ratio to 1 when the angles are aligned (when +110° is reached). With this method, because the rotational joint 8a is always moved in accordance with the operation of the dial 18e, it is possible to allow the operator to perform the operation without causing him/her to become aware of an abnormality.

In addition, in the case in which initialization is performed without performing a special operation with regard to the correspondence relationship between the rotational joint 8a and the dial 18e, the rotational joint 8a is moved by decreasing the motion-scale ratio of the rotational joint 8a with respect to the dial 18e until the limit sensor 31 detects the limit of the rotational-angle range of the dial 18e for the first time; and, in the case in which the limit sensor 31 has detected the limit, the angle of the rotational joint 8a at that time is acquired, and the rotational joint 8a is not moved regardless of the rotation of the dial 18e until the alignment with the acquired angle of the rotational joint 8a is achieved.

Figure 25:
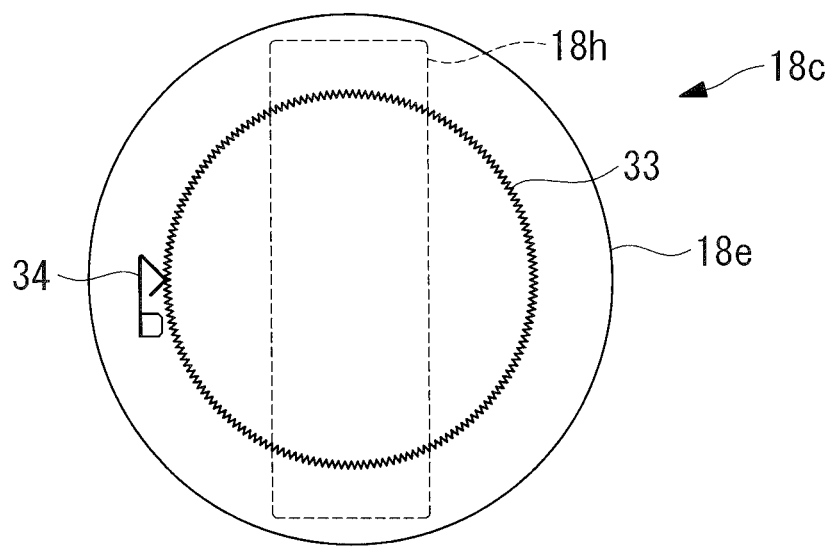
FIG. 25 is a diagram showing an example of a structure that prevents excessive turning of the dial.

In addition, in order to prevent rapid rotation of the dial 18e due to the operation by the operator, resistance may be imparted to the rotation of the dial 18e, for example, by pressing a plate spring 34 provided in the gripping portion 18a against a gear 33 provided in the dial 18e, as shown in FIG. 25.

Figure 26:
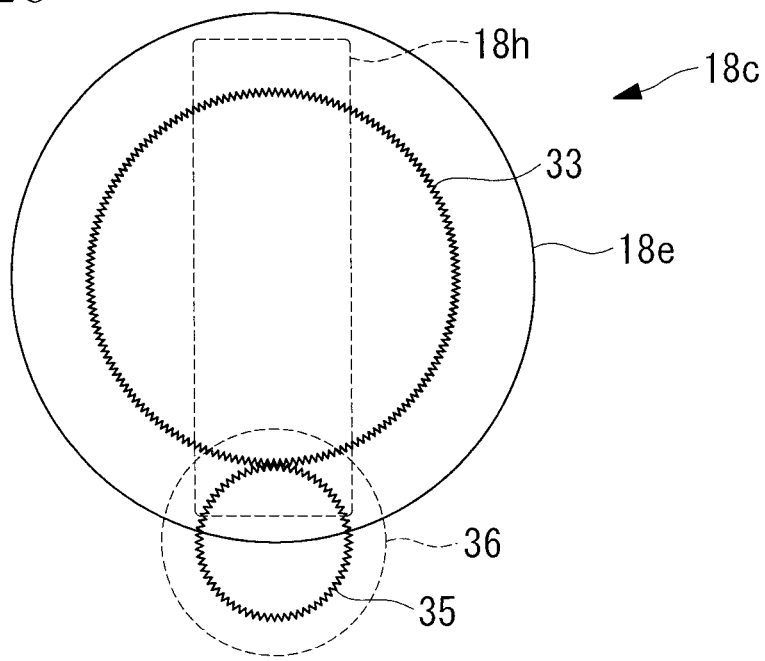
FIG. 26 is a diagram showing an example of a structure that precisely detects the rotational angles of the dial.

In addition, in order to precisely detect the rotational angle of the dial 18e, as shown in FIG. 26, by providing a rotation sensor 36 at a small gear 35 that engages with the gear 33 provided in the dial 18e, the resolution may be enhanced by accelerating the rotation of the rotation sensor 36 relative to that of the dial 18e.

Figure 27:
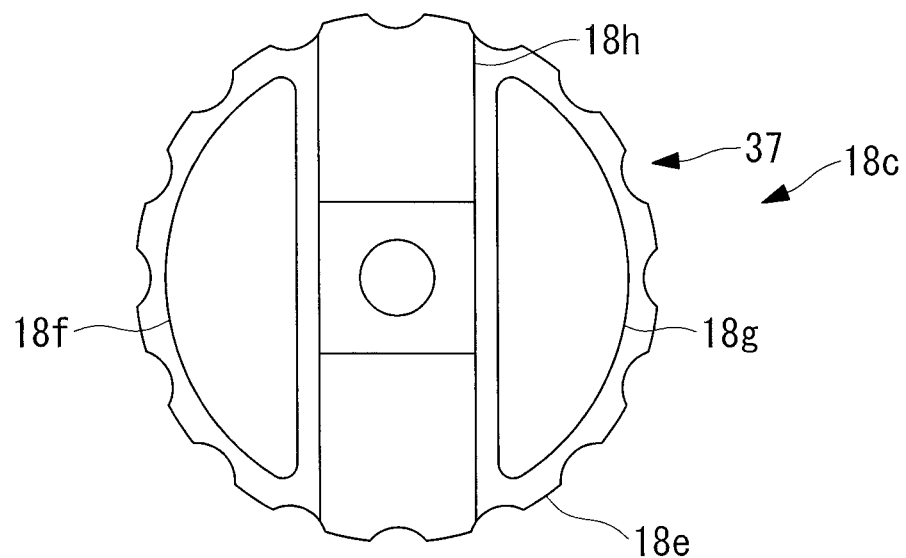
FIG. 27 is a diagram showing an example of a structure for enhancing the ease of turning the dial.

In addition, in order to allow the operator to more easily rotate the dial 18e, gripping with the fingers may be facilitated by providing irregularities 37 in the periphery of the dial 18e, as shown in FIG. 27.

Figure 28:
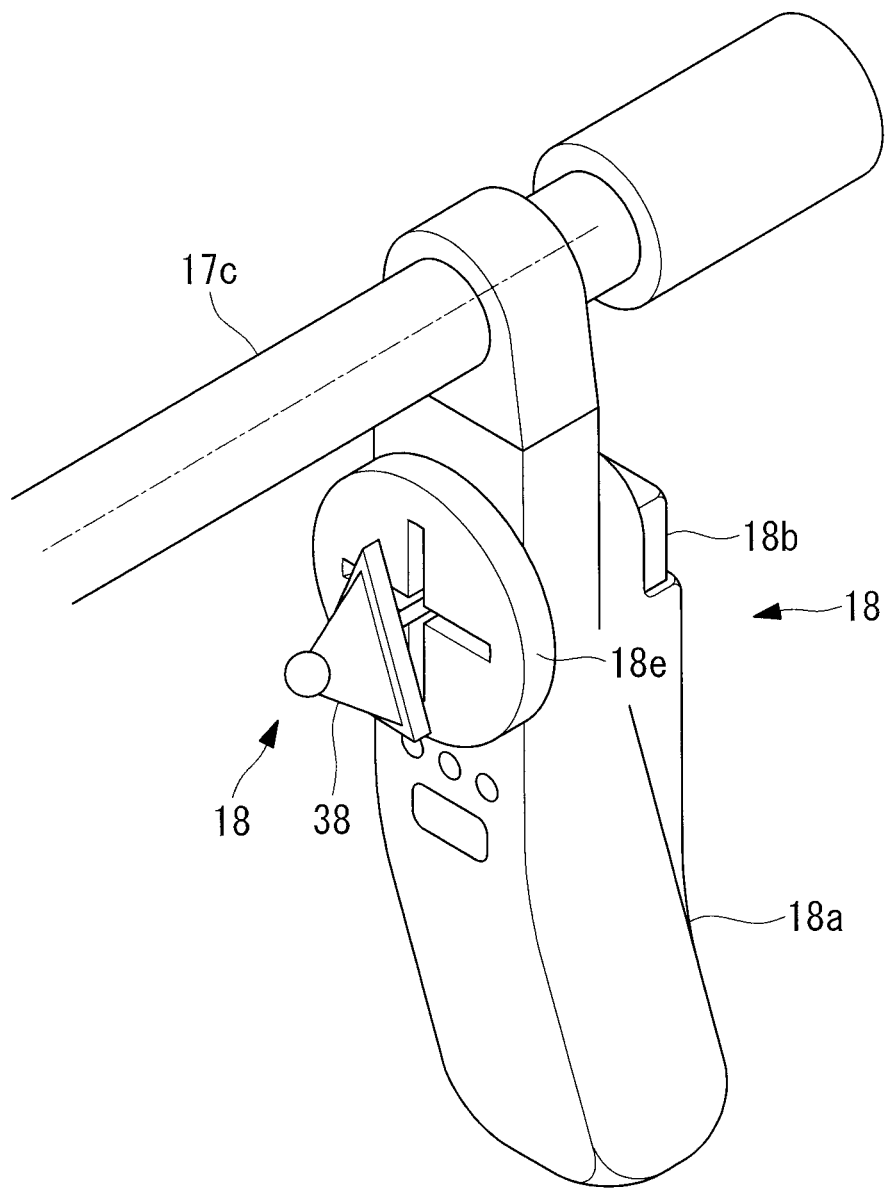
FIG. 28 is a perspective view showing a ninth modification of the surgical-manipulator operating device in FIG. 3.

In addition, in this embodiment, although the electric operation portion 18 is secured to the movable portion 17c so that the dial 18e faces the proximal-end side of the flexible portion 14, as shown in FIG. 4, alternatively, the electric operation portion 18 may be secured to the movable portion 17c so that the dial 18e faces the distal-end side of the flexible portion 14, as shown in FIG. 28.

In the example illustrated in FIG. 28, a joystick-type switch 38 for operating the two flexing joints 8b and 8c is provided.

By doing so, the dial 18e is rotated by the thumb of the hand that is gripping the gripping portion 18a, and the switch 38 is operated by the index finger and the middle finger thereof. In this case, while the arrangements of the joints 8a to 8c in the multi-joint treatment tool 8 are such that the rotational joint 8a is arranged on the proximal-end side, and the two flexing joints 8b and 8c are arranged on the distal-end side, because the arrangements in the electric operation portion 18 are also such that the dial 18e for operating the rotational joint 8a is arranged on the proximal-end side and the switch 38 for operating the flexing joints 8b and 8c is arranged on the distal-end side, the operator can experience an operational feeling that is as if he/she is operating the multi-joint treatment tool 8 by gripping the multi-joint treatment tool 8.

Figure 29:
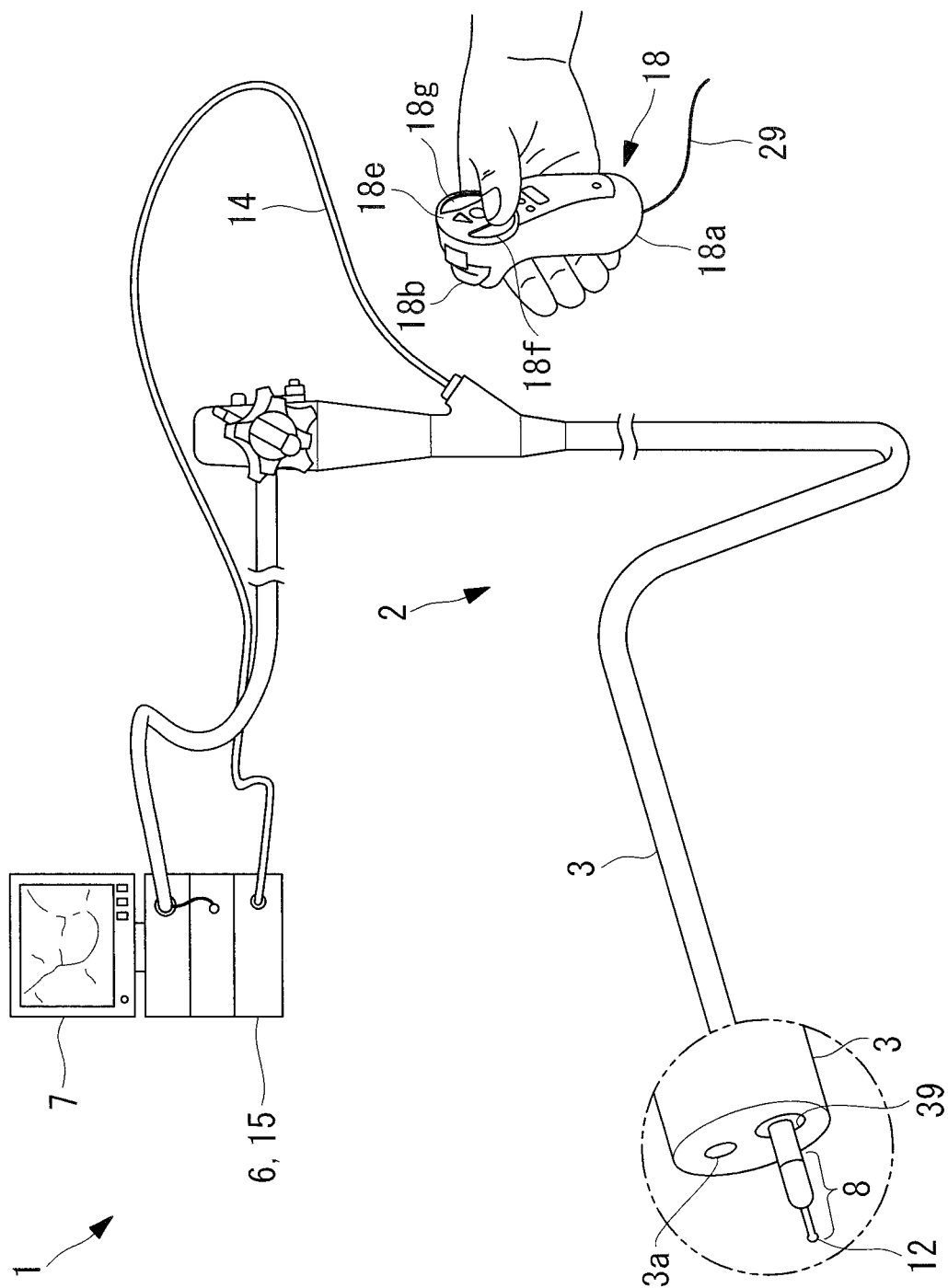
FIG. 29 is an overall configuration diagram showing a modification of the surgical-manipulator system in FIG. 1.

In addition, in this embodiment, although the multi-joint treatment tool 8 of the manipulator 4 secured to the inserted portion 3 by using the securing tool 3b is operated by using the electric operation portion 18 secured to the movable portion 17c of the manual operation portion 17, alternatively, as shown in FIG. 29, the flexible portion 14 that is introduced via a channel 39 provided in the inserted portion 3 of the endoscope 2 may be pushed and pulled by the hand gripping the electric operation portion 18 on the proximal-end side of the inserted portion 3.

Figure 30:
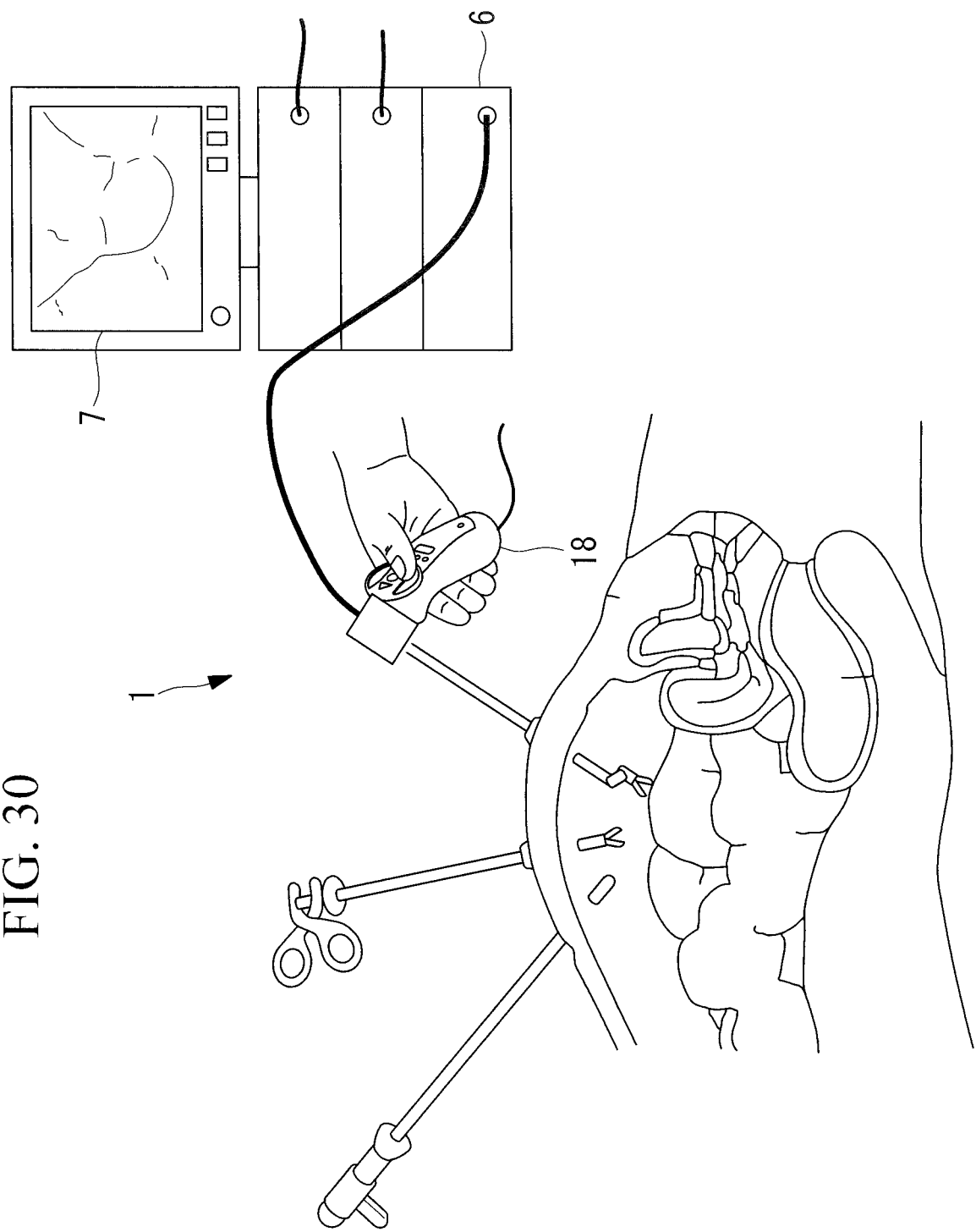
FIG. 30 is an overall configuration diagram showing another modification of the surgical-manipulator system in FIG. 1.

In addition, without limitation to surgery in which the endoscope 2 is employed, as described in this embodiment, the present invention can be applied to a treatment tool employed in laparoscopic surgery, as shown in FIG. 30.

In addition, in this embodiment, although the movable portion 17c to which the flexible portion 14 is secured is manually moved in the longitudinal-axis direction, alternatively, a linear motion device (not shown) that electrically moves the flexible portion 14 in the longitudinal-axis direction may be provided, the electric operation portion may also be supported by the linear motion mechanism in a movable manner, and the linear motion device may be controlled by detecting the amount by which the electric operation portion is moved.

The above-described embodiment leads to the following inventions.

An aspect of the present invention provides a surgical-manipulator operating device that is a device for operating a surgical manipulator provided with, at a distal end of an elongate shaft, a rotational joint that is rotatable about a longitudinal axis of the shaft, and a flexing joint that is on a distal-end side of the rotational joint and that can be flexed about an axis that intersects the longitudinal axis, the surgical-manipulator operating device including: a gripping portion that is gripped by an operator; a rotation input portion that is provided with a rotating member attached to the gripping portion in a rotatable manner and with which rotation instructions for the rotational joint are input in accordance with rotational angles of the rotating member; and a flexion input portion with which flexion instructions for the flexing joint are input in directions corresponding to fixed circumferential-direction operating positions on the rotating member.

With this aspect, when the operator grips the gripping portion and rotates the rotating member with respect to the gripping portion, the rotational joint provided at the distal end of the shaft is rotated just by rotational angle corresponding to that rotational angle. Because the flexing joint is disposed on the distal-end side of the rotational joint, when the rotational joint is rotated, the flexing joint is also rotated together. As a result, the flexing direction of the flexing joint is changed in association with the rotation of the rotational joint. On the other hand, because the operating positions for inputting the flexion instructions for the flexing joint are fixed in the rotating member, when the rotating member is rotated in order to rotate the rotational joint, the operating positions for inputting the flexion instructions for the flexing joint are also rotated in association with the rotation of the rotating member.

For example, in a state in which the longitudinal axis of the shaft is horizontally arranged, in the case in which the flexing direction of the flexing joint is in the top-to-bottom direction and the operating positions fixed in the rotating member for the flexing joint are disposed at top and bottom thereof, rotating the rotating member clockwise by 45° causes the rotational joint to be rotated clockwise by 45°, and, consequently, the flexing direction of the flexing joint is changed to a 45°-direction on the diagonally right hand side; however, because the operating positions on the rotating member are also rotated to the 45°-direction on the diagonally right hand side, the operator can intuitively understand the correspondence between the operating positions and the flexing directions, and thus, it is possible to input appropriate flexion instructions for flexing the flexing joint without causing confusion.

In the above-described aspect, the flexion input portion may be a switch that is attached to the rotating member and that is rotated together with rotation of the rotating member.

When the rotational joint of the manipulator is rotationally operated by rotating the rotating member of the operating device, the flexing direction of the flexing joint, which is disposed farther on the distal-end side than the rotational joint of the manipulator is, is also rotated. However, because the switch for inputting the flexion instructions, which is attached to the rotating member of the operating device, is also rotated together with the rotating member, by aligning the flexing direction of the flexing joint of the manipulator and the direction of the switch of the operating device for inputting the flexion instructions at the beginning of operation, the flexing direction and the direction of the switch are aligned even if the rotational joint is subsequently operated. Because of this, just by operating the switch, the operator can perform flexing operation of the flexing joint in the directions corresponding to the circumferential-direction positions of the switch. In other words, the operator can intuitively understand the correspondence between the positions of the switch and the flexing directions, and thus, it is possible to input appropriate flexion instructions for flexing the flexing joint without causing confusion.

In addition, in the above-described aspect, the surgical manipulator may be provided with two flexing joints, and the flexion input portions for inputting flexion instructions for different flexing joints may be disposed at different circumferential-direction positions on the rotating member.

In addition, in the above-described aspect, the flexion input portion may include: a plurality of sensors that are secured to the gripping portion, that are arranged in a circumferential direction of the rotating member, and that detect circumferential-direction positions at which the flexion instructions via the rotating member are input; and a signal generating portion that generates flexion instruction signals in accordance with the rotational angles of the rotating member and the positions of the sensors at which the flexion instructions are detected.

By doing so, when the operator performs operation at one of the circumferential-direction positions of the rotating member in order to input the flexion instructions for the flexing joint, that circumferential-direction position is detected by the sensors. Although the operating positions for flexing the flexing joint in specific directions are fixed in the rotating member, because the sensors are secured to the gripping portion, even if the sensor that has detected the circumferential-direction position is the same, the resulting flexion instructions would be for a different direction of the flexing joint in the case in which the rotational angle of the rotating member is different.

Therefore, by generating the flexion instruction signals, by means of the signal-generating portion, on the basis of the rotational angles of the rotating member and the positions of the sensors that have detected the flexion instructions, it is possible to rotate the operating positions for inputting the flexion instructions in accordance with the rotational angles of the rotating member, and thus, it is possible, even if the rotational joint is rotated, to input appropriate flexion instructions for flexing the flexing joint without causing the operator to become confused. In addition, because the sensors are not provided in the rotating member, movable wiring is not necessary, and thus, it is possible to simplify the device configuration.

In addition, in the above-described aspect, the rotating member may be provided so as to be attachable to and detachable from the gripping portion, and the above-described aspect may be provided with a drape having a through-hole that supports the rotating member in a rotatable manner and that covers the entire gripping portion.

By doing so, by attaching the rotating member, which is supported by the through-hole of the drape in a rotatable manner, to the gripping portion in the state in which the entire gripping portion is covered with the drape, it is possible to transmit the rotation of the rotating member to the gripping portion without damaging the drape while preventing, by using the drape, the gripping portion from becoming polluted. By doing so, it is possible to reuse the gripping portion by constituting the drape and the rotating member in a disposable manner.

In addition, in the above-described aspect, the rotating member may be provided, at a surface thereof, with an indicator with which a specific circumferential-direction position of the rotating member can be identified via a tactile sensation.

By doing so, the operator can recognize the state of the rotating member by touching, with a finger, the indicator provided on the surface of the rotating member, and thus, it is possible to input appropriate motion instructions for the rotational joint and the flexing joint via just the tactile sensations without having to visually check the rotating member.

In addition, in the above-described aspect, the gripping portion may be attached to the shaft so that the rotating member faces a proximal-end side of the shaft.

By doing so, the rotation input portion and the flexion input portion can be disposed so as to be aligned with the angle of the rotational joint and the flexing direction of the flexing joint displayed in an endoscope image.

In addition, in the above-described aspect, the gripping portion may be attached to the shaft so that the rotating member faces a distal-end side of the shaft.

By doing so, the rotation input portion and the flexion input portion can be disposed in such a way that even the order of the rotational joint and the flexing joint displayed in an endoscope image are matched. By doing so, it is possible to provide an operational feeling that is as if the rotational joint and the flexing joint of the surgical manipulator are operated by directly gripping them.

In addition, in the above-described aspect, the surgical manipulator may be provided with a moving mechanism that drives a shaft in the longitudinal-axis direction, and the above-described aspect may be provided with a movement input portion with which movement instructions for the moving mechanism are input depending on the amount by which the gripping portion is moved in a front-to-rear direction.

By doing so, by inputting the movement instructions by moving the gripping portion in the front-to-rear direction by using the movement input portion, it is possible to drive the shaft in the longitudinal-axis direction just by distances corresponding to the movement instructions by using the movement input portion.

In addition, another aspect of the present invention provides a surgical-manipulator system provided with any one of the above-described surgical-manipulator operating devices.

REFERENCE SIGNS LIST 1 surgical-manipulator system
8 multi-joint treatment tool (surgical manipulator)
8a rotational joint
8b, 8c flexing joint
14 flexible portion (shaft)
18 electric operation portion (surgical-manipulator operating device)
18a gripping portion
18c second operation input portion (rotation input portion)
18e dial (rotating member)
18f, 18g switch (flexion input portion)
18h protrusion (indicator)
23a to 23d sensor
25 drape
25a through-hole

The invention claimed is:

1. A surgical-manipulator operating device for operating a surgical manipulator including, at a distal end of a shaft elongated along a longitudinal axis, a first joint rotatable about the longitudinal axis of the shaft, and a second joint disposed distally relative to the first joint, the second joint being rotated about the longitudinal axis along with rotation of the rotational joint and rotatable about a first axis orthogonal to the longitudinal axis, the surgical-manipulator operating device comprising:
  a grip configured to be gripped by an operator;
  a dial rotatably attached to the grip about a second axis, the dial comprising one or more switches provided radially offset from the second axis of the dial, the one or more switches being rotated together with the dial;
  wherein a rotation operation of the dial inputs first rotation instructions for the first joint; and
  a pressing operation of the one or more switches inputs second rotation instructions for the second joint.

2. A surgical-manipulator operating device according to claim 1,
  wherein the surgical manipulator is provided with two or more second joints,
  the one or more switches comprise two or more switches each configured to input the second rotation instructions for respective second joints of the two or more second joints; and
  the two or more second switches are disposed at different positions on the dial.

3. A surgical-manipulator operating device according to claim 1, further comprising:
  a plurality of sensors secured to the grip, the plurality of sensors being arranged radially offset from the second axis of the dial, the plurality of sensors being configured to detect rotational angles of the dial relative to the grip; and
  a signal generating portion that generates the first rotation instructions based on the detected rotational angles.

4. A surgical-manipulator operating device according to claim 3,
  wherein the dial is provided so as to be attachable to and detachable from the grip,
  the surgical-manipulator operating device further comprising:
  a drape provided with a through-hole that supports the dial in a rotatable manner and that covers portions of the grip other than the dial.

5. A surgical-manipulator operating device according to claim 1, wherein the dial is provided with an indicator disposed at a surface of the dial, a circumferential-direction position of the dial can be identified via a tactile sensation of the indicator.

6. A surgical-manipulator operating device according to claim 1, wherein the grip is configured to be attached to the shaft so that the dial faces a proximal-end side of the shaft.

7. A surgical-manipulator operating device according to claim 1, wherein the grip is configured to be attached to the shaft so that the dial faces a distal-end side of the shaft.

8. A surgical-manipulator system comprising:
   the surgical manipulator; and
   the surgical-manipulator operating device according to claim 1.

* * * * *